(12) United States Patent  (10) Patent No.: US 7,156,661 B2
Choi et al.  (45) Date of Patent: *Jan. 2, 2007

(54) SYSTEMS AND METHODS FOR TREATMENT ANALYSIS BY TEETH MATCHING

(75) Inventors: Woncheol Choi, San Jose, CA (US); Jihua Cheng, Cupertino, CA (US); Eric Kuo, Foster City, CA (US)

(73) Assignee: Align Technology, Inc., Santa Clara, CA (US)

( * ) Notice: Subject to any disclaimer, the term of this patent is extended or adjusted under 35 U.S.C. 154(b) by 164 days.

This patent is subject to a terminal disclaimer.

(21) Appl. No.: 10/640,439

(22) Filed: Aug. 12, 2003

(65) Prior Publication Data

US 2005/0048432 A1    Mar. 3, 2005

Related U.S. Application Data

(63) Continuation-in-part of application No. 10/225,889, filed on Aug. 22, 2002, now Pat. No. 7,077,647.

(51) Int. Cl.
*A61C 11/00* (2006.01)
*A61C 3/00* (2006.01)

(52) U.S. Cl. ........................... 433/213; 433/24
(58) Field of Classification Search ............ 433/24, 433/213
See application file for complete search history.

(56) References Cited

U.S. PATENT DOCUMENTS

| | | | |
|---|---|---|---|
| 2,467,432 A | 4/1949 | Kesling | |
| 3,660,900 A | 5/1972 | Andrews | |
| 3,860,803 A | 1/1975 | Levine | |
| 3,916,526 A | 11/1975 | Schudy | |
| 3,950,851 A | 4/1976 | Bergersen | |
| 4,014,095 A | 3/1977 | Dellinger | |
| 4,195,046 A | 3/1980 | Kesling | |
| 4,324,546 A | 4/1982 | Heitlinger et al. | |
| 4,348,178 A | 9/1982 | Kurz | |
| 4,478,580 A | 10/1984 | Barrut | |
| 4,504,225 A | 3/1985 | Yoshii | |
| 4,505,673 A | 3/1985 | Yoshii | |
| 4,575,805 A | 3/1986 | Moermann et al. | |
| 4,611,288 A | 9/1986 | Duret et al. | |
| 4,656,860 A | 4/1987 | Orthuber et al. | |
| 4,663,720 A | 5/1987 | Duret et al. | |

(Continued)

FOREIGN PATENT DOCUMENTS

EP    091876 A1    10/1983

(Continued)

OTHER PUBLICATIONS

Woncheol Choi and T.R. Kurfess, "Dimensional Measurement Data Analysis, Part 1: A Zone Fitting Algorithm" Transactions of the ASME (May 1999, vol. 121) pp. 238-245.

(Continued)

*Primary Examiner*—John J Wilson
(74) *Attorney, Agent, or Firm*—Greenberg Traurig, LLP; David C. Cohen

(57) ABSTRACT

Systems and methods are disclosed for matching computer models of two sets of teeth each having corresponding matching regions includes calculating a difference for two sets of teeth shapes; finding the position of one set of teeth with respect to the other set of teeth; calculating a positional difference of the corresponding teeth based on the matching regions; and finding a corrective path to bring one set of teeth to the other set of teeth.

26 Claims, 15 Drawing Sheets

U.S. PATENT DOCUMENTS

| | | | |
|---|---|---|---|
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,837,732 A | 6/1989 | Brandestini et al. |
| 4,850,864 A | 7/1989 | Diamond |
| 4,856,991 A | 8/1989 | Breads et al. |
| 4,936,862 A | 6/1990 | Walker et al. |
| 4,937,928 A | 7/1990 | van der Zel |
| 4,964,770 A | 10/1990 | Steinbichler et al. |
| 4,975,052 A | 12/1990 | Spencer et al. |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,128,870 A | 7/1992 | Erdman et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| 5,518,397 A | 5/1996 | Andreiko et al. |
| 5,533,895 A | 7/1996 | Andreiko et al. |
| 5,542,842 A | 8/1996 | Andreiko et al. |
| 5,549,476 A | 8/1996 | Stern |
| 5,587,912 A | 12/1996 | Andersson et al. |
| 5,605,459 A | 2/1997 | Kuroda et al. |
| 5,607,305 A | 3/1997 | Andersson et al. |
| 5,645,421 A | 7/1997 | Slootsky |
| 5,655,653 A | 8/1997 | Chester |
| 5,683,243 A | 11/1997 | Andreiko et al. |
| 5,733,126 A | 3/1998 | Andersson et al. |
| 5,740,267 A | 4/1998 | Echerer et al. |
| 5,975,893 A | 11/1999 | Chishti et al. |
| 6,068,482 A | 5/2000 | Snow |
| 6,227,850 B1 | 5/2001 | Chishti et al. |
| 6,227,851 B1 | 5/2001 | Chishti et al. |
| 6,250,918 B1 | 6/2001 | Sachdeva et al. |
| 6,371,761 B1 | 4/2002 | Cheang et al. |
| 6,540,512 B1 | 4/2003 | Sachdeva et al. |
| 6,733,289 B1 | 5/2004 | Manemann et al. |
| 2001/0034010 A1 | 10/2001 | MacDougald et al. |

FOREIGN PATENT DOCUMENTS

| | | |
|---|---|---|
| EP | 299490 A2 | 1/1989 |
| EP | 376873 A2 | 7/1990 |
| EP | 490848 B1 | 6/1992 |
| EP | 774933 B1 | 5/1997 |
| EP | 541500 A1 | 6/1998 |
| EP | 731673 B1 | 9/1998 |
| FR | 2369828 A1 | 8/1978 |
| FR | 2652256 A1 | 3/1991 |
| WO | WO 90/08512 A1 | 8/1990 |
| WO | WO 91/04713 A1 | 4/1991 |
| WO | WO 94/10935 A1 | 5/1994 |
| WO | WO 98/44865 A1 | 10/1998 |
| WO | WO 98/58596 A1 | 12/1998 |

OTHER PUBLICATIONS

Woncheol Choi and T.R. Kurfess,"Dimensional Measurement Data Analysis, Part 2: Minimum Zone Evaluation" Transactions of the ASME (May 1999, vol. 121) pp. 246-250.

Z.X. Li, J. Gou and Y. Chu, "Geometric Algorithms for Workpiece Localization", Dept. of Electrical and Electronic Engineering Hong Kong Univ. of Science and Technology (May 21, 1997) pp. 1-30.

Alexander et al., "The DigiGraph Work Station Part 2, Clinical Management," *JCO*(Jul. 1990), pp. 402-407.

Altschuler et al., "Laser Electro-Optic System for Rapid Three-Dimensional (3D) Topographic Mapping of Surfaces," *Optical Engineering*, vol. 20(6) (1981), pp. 953-961.

Altschuler et al, "Measuring Surfaces Space-Coded by a Laser-Projected Dot Matrix," *SPIE Imaging Applications for Automated Industrial Inspection and Assembly*, vol. 182 (1979), p. 187-191.

Atlschuler et al., "Analysis of 3-D Data for Comparative 3-D Serial Growth Pattern Studies of Oral-Facial Structures," Program and Abstracts of Papers, Feb. 1975, *Journal of Dental Research*, vol. 54, IADR Abstracts 1979, 2 pages total.

Altschuler, "3D Mapping of Maxillo-Facial Prosthesis," AADR Abstract #607, 1980, 2 pages total.

American Association for Dental Research, Summary of Activities, Mar. 20-23, 1980, Los Angeles, CA, p. 195.

Andersson et al., "Clinical Results with Titanium Crowns Fabricated with Machine Duplication and Spark Erosion," *Acta Odontological Scandinavia*, vol. 47 (1989), pp. 279-286.

Baumrind et al., "A stereophotogrammetric system for the detection of prosthesis loosening in total hip arthroplasty, Applications of Human Biostereometrics (NATO)," Proceedings of the Society of Photo-Optical Instrumentation Engineers, vol. 166, Jul. 9-13, 1978, pp. 112-123.

Baumrind et al., Mapping the Skull in 3-D, Reprinted from The Journal, *California Dental Association*, vol. 48, No. 2 (1972 Fall Issue) 11 pages total.

Baumrind et al., "Seminars in Orthodontics," *Seminars in Orthodontics*, vol. 7, No. 4 (Dec. 2001), p. 222.

Baumrind, "A System for Craniofacial Mapping Through the Integration of Data from Stereo X-Ray Films and Stereo Photographs," An invited paper submitted to the 1975 American Society of Photogram. Symposium on Close-Range Photogram. Systems, University of Ill., Aug. 26-30, 1975, pp. 1-25.

Baumrind, "Integrated Three-Dimensional Craniofacial Mapping: Background, Principles, and Perspectives," *Seminars in Orthodontics*, vol. 7, No. 4 (Dec. 2001), pp. 223-232.

Begole et al., "A Computer System for the Analysis of Dental Casts," *The Angle Orthodontist*, vol. 51 No. 3 (Jul. 1981), pp. 253-259.

Bernard et al., "Computerized diagnosis in Orthodontics for Epidemiological Studies" (progress report), Abstracts of Papers, *Journal of Dental Research*; vol. 71, Special Issue Mar. 1-14, 1992, pp. 28-36.

Bhatia et al., "A Computer-Aided Design for Orthognathic Surgery," *British Journal of Oral and Maxillofacial Surgery*, vol. 22 (1984), pp. 237-253.

Biggerstaff et al., "Computerized analysis of occlusion in the postcanine dentition," *American Journal of Orthodontics*, vol. 61, No. 3 (Mar. 1972), pp. 245-254.

Biggerstaff, "Computerized Diagnostic Setups and Simulations," *The Angle Orthodontist*, vol. 40, No. 1 (Jan. 1970), pp. 28-36.

Brandestini et al., "Computer Machined Ceramic Inlays: In Vitro Marginal Adaptation," *Journal of Dental Research*, vol. 64/Special Issue/Abstracts, IADR/AADR Abstracts 1985, 1 page total.

Brook et al., An Image Analysis System for the Determination of Tooth Dimensions from Study Casts: Comparison with Manual Measurements of Mesio-distal Diameter, Abstract of Papers, 1985, Dept. of Children's Dentistry and Orthodontics, *J Dent Res.*, Mar. 1986, pp. 428-431.

Burstone (interview), "Dr. Charles J. Burstone on The Uses of the Computer in Orthodontic Practice (Parts 1 and 2)," *Journal of Clinical Orthodontics*, (Part 1) vol. 8, No. 7 , Jul. 1979; (Part 2) vol. 8, No. 8 pp. 539-551, Aug. 1979.

Burstone et al., "Precision adjustment of the transpalatal lingual arch: Computer arch form predetermination," *Am. Journal of Orthodontics*, vol. 79, No. 2 (Feb. 1981), pp. 115-133.

Chaconas et al., "The DigiGraph Work Station, Part 1, Basic Concepts," *JCO* (Jun. 1990), pp. 360-367.

Chafetz et al., "Subsidence of the Femoral Prosthesis, A Stereophotogrammetric Evaluation," *Clinical Orthopedics and Related Research*, No. 201 (Dec. 1985), pp. 60-67.

Chiappone, "Constructing the gnathologic setup and positioner" *J. Clin. Orthod.*, 14:121-133, 1980.

Cottingham, "Gnathologic clear plastic positioner" *Am. J. Orthod.*, 55:23-31, 1969.

Crawford, "Computers in Dentistry: Part 1: CAD/CAM: The Computer Moves Chairside," "Part 2: F. Duret—A Man With A Vision," "Part 3: The Computer Gives New Vision- Literally," "Part 4: Bytes 'N Bites" The Computer Moves From The Front Desk To The Operatory, *Canadian Dental Journal*, vol. 54(9),, (1988), pp. 661-666.

Crawford, "CAD/CAM in the Dental Office: Does It Work?" *Canadian Dental Journal*, vol. 57, No. 2 (Feb. 1991), pp. 121-123.

Crooks, "CAD/CAM Comes to USC," *USC Dentistry*, (Spring 1990) pp. 14-17.

Cureton, "Correcting malaligned mandibular incisors with removable retainers" *J. Clin. Orthod.*, 30:390-395, 1996.

Curry et al., "Integrated Three-Dimensional Craniofacial Mapping at the Craniofacial Research Instrumentation Laboratory/University of the Pacific," *Seminars in Orthodontics*, vol. 7, No. 4 (Dec. 2001), pp. 258-265.

Cutting et al., "Three-Dimensional Computer-Assisted Design of Craniofacial Surgical Procedures: Optimization and Interaction with Cephalometric and CT-Based Models," *Plastic and Reconstructive Surgery*, vol. 77, No. 6 (Jun. 1986), pp. 877-885.

DCS Dental AG, "The CAD/CAM 'DCS Titan System' for Production of Crowns/Bridges" *DSC Production AG*, Jan. 1992, pp. 1-7.

Defranco et al., "Three-Dimensional Large Displacement Analysis of Orthodontic Appliances," *J. Biomechanics*, vol. 9 (1976), pp. 793-801.

Dental Institute University of Zurich Switzerland, Program for International Symposium on Computer Restorations: State of the Art of the CEREC-Method, May 1991, 3 pages total.

DenTrac Corporation, Dentrac document, pp. 4-13.

Duret et al, "CAD-CAM in Dentistry," *Journal of the American Dental Association*, vol. 117 (Nov. 1988), pp. 715-720.

Duret et al., "CAD/CAM imaging in dentistry," *Current Opinion in Dentistry*, vol. 1 (1991), pp. 150-154.

Duret, "The Dental CAD/CAM, General Description of the Project," *Hennson International Product Brochure*, Jan. 1986, 18 pages total.

Duret, "Vers une prosthese informatisee," (English translation also attached), *Tonus*, vol. 75, (Nov. 15, 1985), pp. 55-57.

Economides, "The Microcomputer in the Orthodontic Office," *JCO*, (Nov. 1979), pp. 767-772.

Elsasser, "Some observations on the history and uses of the Kesling positioner" *Am. J. Orthod.*, 36:368-374, 1950.

Faber et al., "Computerized interactive orthodontic treatment planning," *Am. J. Orthod.*, vol. 73, No. 1 (Jan. 1978), pp. 36-46.

Felton et al. "A computerized analysis of the shape and stability of mandibular arch form," *Am. Journal of Orthodontics and Dentofacial Orthopedics*, vol. 92, No. 6 (Dec. 1987), pp. 478-483.

Friede et al., "Accuracy of Cephalometric Prediction In Orthognathic Surgery," Abstract of Papers, *Journal of Dental Research*, vol. 70 (1987), pp. 754-760.

Gim-Alldent Deutschland, "Das DUX System: Die Technik" 4 pages total.

Grayson, "New Methods for Three Dimensional Analysis of Craniofacial Deformity," Symposium: Computerized Facial Imaging in Oral and Maxilofacial Surgery, AAOMS Sep. 13, 1990, 3 pages total.

Guess et al., "Computer Treatment Estimates in Orthodontics and Orthognathic Surgery," *JCO*, (Apr. 1989), pp. 262-28.

Heaven et al., "Computer-based Image Analysis of Artificial Root Surface Caries," "Automated Identification of Landmarks in Cephalometric Radiographs," Abstracts of Papers, *Journal of Dental Research*, vol. 67, Mar. 9-13, 1988, 2 pages total.

Hoffmann et al., "Role of Cephalometry for Planning of Jaw Orthopedics and Jaw Surgery Procedures," (Article Summary in English, article in German), *Informationen*, (Mar. 1991), pp. 375-396.

Huckins, "CAD-CAM Generated Mandibular Model Prototype from MRI Data," *AAOMS* 1999, p. 96.

Inside the ADA, *Journal Of The American Dental Assoc.*, vol. 118 (Mar. 1989) 9 pages total.

JCO Interviews, "Craig Andreiko, DDS, MS on the Elan and Orthos Systems,", JCO, (Aug. 1994), pp. 459-468.

JCO Interviews, "Dr. Homer W. Phillips on Computers in Orthodontic Practice, Part 2," JCO, (Dec. 1983), pp. 819-831.

Jerrold, "The problem, electronic data transmission and the law," *AJO-DO*, (Apr. 1988), pp. 478-479.

Jones et al., "An Assessment of the Fit of a Parabolic Curve to Pre- and Post-Treatment Dental Arches," *British Journal of Orthodontics*, vol. 16 (1989), pp. 85-93.

Kamada et al., "Case reports on tooth positioners using LTV vinyl silicone rubber" J. Nihon University School of Dentistry, 26(1):11-29, 1984.

Kamada et al., "Construction of tooth positioners with LTV vinyl silicone rubber and some case reports" J. Nihon University School of Dentistry, 24(1):1-27, 1982.

Kanazawa et al., "Three-Dimensional Measurements of the Occlusal Surfaces of Upper Molars in a Dutch Population," *J. Dent Res.*, vol. 63, No. 11 (Nov. 1984), pp. 1298-1301.

Kesling, "Coordinating the predetermined pattern and tooth positioner with conventional treatment" *Am. J. Orthod. Oral. Surg.*, 32:285-293, 1946.

Kesling, "The philosophy of the tooth positioning appliance" *Am. J. Orthod. Oral. Surg.*, 31(6):297-304, 1945.

Kleemann et al., "The speed positioner" *J. Clin. Orthod.*, 30:673-680, 1996.

Kuroda et al., "Three-dimensional dental cast analyzing system using laser scanning" *Am. J. Orthod. Dentofac. Orthop.*, 110:365-369, 1996.

Laurendeau et al., "A Computer-Vision Technique for the Acquisition and Processing of 3-D Profiles of Dental Imprints: An Application in Orthodontics," *IEEE Transactions on Medical Imaging*, vol. 10, No. 3 (Sep. 1991), pp. 453-461.

Leinfelder et al., "A new method for generating ceramic restorations: a CAD-CAM system," *Journal Of The American Dental Assoc.*, vol. 118, No. 6 (Jun. 1989), pp. 703-707.

McNamara et al., *Orthodontic and Orthopedic Treatment in the Mixed Dentition*, Needham Press, Jan. 1993, pp. 347-353.

McNamara et al., "Invisible Retainers", *J. Clinical Orthodontics*, (Aug. 1985) pp. 570-578.

Moermann et al., "Computer Machined Adhesive Porcelain Inlays: Margin Adaptation after Fatigue Stress," IADR Abstract 339, *Journal of Dental Research*, vol. 66(a) (1987), p. 339.

Mörmann et al., "Marginal Adaptation von adhasiven Porzellaninlays in vitro," *Schwizerische Monatsschrift fur Zahnmedizin*, vol. 85 (1985), p. 1118-1129.

Mörmann et al., "Marginale Adaptation von adhäsuven Porzellaninlays in vitro," Separatdruck aus: Schweiz. Mschr. Zahnmed. 95: 1118, 1985.

Nahoum, "The vacuum formed dental contour appliance" *The New York State Dental Journal*, 30(9):385-390, Nov. 1964.

Nash, "CEREC CAD/CAM Inlays: Aesthetics and Durability in a Single Appointment," *Dentistry Today*, (Oct. 1990), pp. 20, 22-23, 54.

Nishiyama et al., "A new construction of tooth repositioner by LTV vinyl silicone rubber" J. Nihon University School of Dentistry, 19(2):93-102, 1977.

Pinkham, "'Foolish' Concept Propels Technology," *Dentist*, Jan./Feb. 1989, 3 pages total.

Pinkham, "Inventor's CAD/CAM may transform dentistry," *Dentist*, Sep. 1990, 3 pages total.

Ponitz, Invisible Retainers, 59 *Am. J. Orthodontics*, Mar. 1971, pp. 266-272.

Procera Research Projects, *PROCERA Research Projects* 1993—Abstract Collection, 1993, pp. 3-28.

Rekow, "A Review of the Developments in Dental CAD/CAM Systems," (contains references to Japanese efforts and content of the papers of particular interest to the clinician are indicated with a one-line summary of their content in the bibliography), Dental Clinics: *Prosthodontics and Endodontics*, pp. 25-33, 1992.

Rekow, "CAD/CAM in Dentistry: A Historical Perspective and View of the Future," *Journal*, vol. 58 No. 4, (Apr. 1992), pp. 283, 287-288.

Rekow, "Computer-Aided Design and Manufacturing in Dentistry: A Review of the State of the Art," *The Journal of Prosthetic Dentistry*, vol. 58, No. 4 (Oct. 1987), pp. 512-516.

Rekow, "Dental CAD-CAM Systems: What is the State of the Art?" *Journal of the American Dental Assoc.*, vol. 122 (1991), pp. 43-48.

Rekow, "Feasibility of an Automated System for Production of Dental Restorations," PhD Thesis, Univ. of Minnesota, Nov. 1988, 244 pages total.

Richmond et al., Research Reports, "The development of a 3D Cast Analysis System," *British Journal of Orthodontics*, pp. 53-54.

Richmond, "Recording the dental cast in three dimensions," *Am. J. Orthod. Dentofac. Orthop.*, vol. 92, No. 3, (Sep. 1987), pp. 199-206.

Rudge, "Dental arch analysis: arch form, A review of the literature," *European Journal of Orthodontics*, vol. 3, No. 4 (1981), pp. 279-284.

Sakuda et al., "Integrated information-processing system in clinical orthodontics: An approach with use of a computer network system," *Am. J. Orthod. Dentofac. Orthop.* vol. 101 No. 3 (Mar. 1992), pp. 210-220.

Schellhas et al., "Three-Dimensional Computer Tomography in Maxillofacial Surgical Planning," *Arch Otolamgol Head Neck Surg.* vol. 114 (Apr. 1988), pp. 438-442.

Segu et al., "Computer-aided Cefalometry and New Mechanics in Orthodontics" (Article Summary in English, article in German), *Fortschr. Kieferorthop.* 44, 370-376 (Nr. 5), 1983.

Shilliday, "Minimizing finishing problems with the mini-positioner" *Am. J. Orthod.* 59:596-599, 1971.

Siemens, "CEREC—Computer-Reconstruction," High Tech in der Zahnmedizin, 14 page total.

Sirona Dental Systems GmbH, CEREC 3D, Manuel utilisateur, Version 2.0X (in French), 2003, 114 pages total.

Stoll et al., "Computer-aided Technologies in Dentistry" (Article Summary in English, article in German), *Dtsch Zahnärztl Z* 45, 314-322, 1990.

U.S. Department of Commerce, National Technical Information Service, "Automated Crown Replication Using Solid Photography SM," Solid Photography Inc. Melville NY, Oct. 1977, 21 pages total.

U.S. Department of Commerce, National Technical Information Service, "Holodontography: An Introduction to Dental Laser Holography," School of Aerospace Medicine Brooks AFB Tex, Mar. 1973, 37 pages total.

Van Der Linden et al., Three-Dimensional Analysis of Dental Casts by Means of the Optocom, *J Dent Res*, Jul.-Aug. 1972, p. 1101.

Van Der Linden, "A New Method to Determine Tooth Positions and Dental Arch Dimensions," Jul.-Aug. 1972, p. 1104.

Van Der Zel, "Ceramic-fused-to-metal Restorations with a New CAD/CAM System," *Quintessence International*, vol. 24(11) (1993), pp. 769-778.

Varady et al., "Reverse Engineering of Geometric Models—An Introduction," May 13, 1996, pp. 1-28.

Warunek et al., "Clinical use of silicone elastomer appliances" *JCO*, MH (10):694-700, 1989.

Warunek et al. "Physical and mechanical properties of elastomers in orthodontic positioners" *Am. J. Orthod. Dentofac. Orthop.*, 95:388-400, 1989.

Wells, "Application of the positioner appliance in orthodontic treatment" *Am. J. Orthodont.*, 58:351-366, 1970.

Williams, "Dentistry and CAD/CAM: Another French Revolution," *Journal of Dental Practice Admin.*, Jan./Mar. 1987, pp. 2-5.

Williams, "The Switzerland and Minnesota Developments in CAD/CAM," *Journal of Dental Practice Admin.*, pp. 50-55, Apr./Jun. 1987.

Wishan, "New Advances in Personal Computer Applications for Cephalometric Analysis, Growth Prediction, Surgical Treatment Planning and Imaging Processing, "Symposium: Computerized Facial Imaging in Oral and Maxilofacial Surgery, AAOMS, Sep. 13, 1990, p. 5.

Yamamoto et al., "Three-Dimensional Measurement of Dental Cast Profiles and Its Applications to Orthodontics," Annual Int'l Conf. of IEEE Engineering in Medicine and Biology Society, vol. 12, No. 5, pp. 2051-2053, 1990.

Yamamoto et al., "Optical measurement of dental cast profile and application to analysis of three-dimensional tooth movement in orthodontics," *Frontiers in Med. and Biol. Eng'g*, vol. 1, No. 2 (1988), pp. 119-130.

Boyd et al., "Three Dimensional Diagnosis and Orthodontic Treatment of Complex Malocclusions Wlith the Invisalign Appliance", *Seminars in Orthodontics*, vol. 7, No. 4 (Dec. 2001), p. 274-293.

Manetti et al., "Computer-aided Cefalometry and New Mechanics in Orthodontics" (Article Summary in English, article in German), *Fortschr. Kieferorthop.* 44, 370-376 (Nr. 5), 1983.

McCann, Inside the ADA, *Journal Of The American Dental Assoc.*, vol. 118 (Mar. 1989) pp. 286-294.

McNamara et al., Chapter 19: Invisible Retainers, *Orthodontic and Orthopedic Treatment in the Mixed Dentition*, Needham Press, Jan. 1993, pp. 347-353.

SYSTEMS AND METHODS FOR TREATMENT ANALYSIS BY TEETH MATCHING

The present invention is a continuation in part of U.S. application Ser. No. 10/225,889, filed on Aug. 22, 2002, now U.S. Pat. No. 7,077,647, and assigned to the assignee of the present invention, the content of which is hereby incorporated by reference.

BACKGROUND

The present invention is related generally to the field of orthodontics, and more particularly to systems and methods for measurement of teeth movements.

One objective in orthodontics is to move a patient's teeth to positions where the teeth function optimally and aesthetically. Conventionally, appliances such as braces are applied to the teeth of the patient by an orthodontist. Each appliance exerts continual force on the teeth and gradually urges the teeth toward their ideal positions. Over a period of time, the orthodontist adjusts the appliances to move the teeth toward their final destination.

Generally, the orthodontist specifies in a prescription the final tooth arrangement. The prescription is based on the orthodontist's knowledge and experience in selecting the intended final position of each tooth. The process of attaching the braces to teeth is tedious and painful to the patient. Additionally, each visit reduces the "chair-time" available to the orthodontist that could be used for another patient. Hence, the process of treating teeth using braces can be expensive.

Traditionally, dentists depend on manual measurement to measure dental features and orthodontic properties. They use rulers on teeth impression or X-rays images. Such manual measurements have limitations because they are manual processes and two dimensional measurements. Thus, the measurement results are not very precise and the rotation is difficult to measure. Orthodontists have also used serial head films to describe changes in tooth movement in the anterior-posterior and vertical dimensions. This technique has several limitations. These limitations include: radiation to the patient, magnification errors, operator errors, and stable and reliable anatomic reference points. Rugae change a little over the course of treatment and so indexes used for palatal matching be it drawings or solid impressions of rugae become less reliable.

SUMMARY OF THE INVENTION

The present invention includes a system, apparatus and computer-implemented method for analyzing an orthodontic treatment by using computer models of teeth.

In one aspect, a method for matching computer models of two sets of teeth includes calculating a difference for two sets of teeth shapes; finding the position of one set of teeth with respect to the other set of teeth; calculating a positional difference of the corresponding teeth; and finding a corrective path to bring one set of teeth to the other set of teeth.

Implementations of the above aspect may include one or more of the following. The calculation of a difference can include calculating and displaying shape difference for each tooth of the jaw; and identifying a corresponding location for each shape difference. Finding the position can include placing two jaw impressions in a single coordinate system; selecting a positioning reference; and determining a positional difference for each of the corresponding teeth in the jaw impression. The method can also include matching two impressions of a jaw having teeth thereon; calculating proclination, extrusion, distalization of the teeth; and calculating rotation and orientation changes of the teeth. Moreover, the method can also include finding a correction path from current teeth positions to planned treatment teeth positions.

The advantage of the system includes one or more of the following. With the digital model, precise measurement and movement analysis can be performed. Using three-dimensional rigid body analysis accurate and complete movement of a tooth or the entire jaw can be calculated. Using the digital models, one can get a precise and complete analysis of treatment. The complete analysis can be achieved by taking two digital models, one before treatment and one after treatment, superimposing them in a virtual space, and calculating the movement of each tooth. The system provides an accurate teeth matching and jaw matching results. It reveals the shape difference between two different sets of impressions from the same teeth. It can provide a complete rigid body movement, three translations and three rotations, for each and every tooth. The system provides virtual treatment planning, which has several benefits. Using a virtual treatment plan, the clinician can evaluate treatment options in detail before beginning treatment. It can also serve as a constant objective reference during office visits so that planned treatment goals can be kept visible. The virtual treatment model can also serve as a motivating tool. The clinician can show the virtual model to the patient during office visits to allow the patient to continually see where the treatment is ultimately going.

The system allows the creation of accurate tooth geometry and a gingival model from scanned geometry. It provides feedback and interactivity to a user during the model creation and virtual treatment planning, which can allow the user to make informed decisions about the treatment plan in the process of creating it. Having the ability to simply and reliably compare treatment outcomes to treatment plans can allow the detailed study of many cases.

For treatment outcome analysis, good matching to the surfaces in the rugae area rather than relying on user selections could possibly allow more accurate and repeatable measurements to be made. Using other non-tooth areas in the mouth such as parts of the gingiva surface which tend not to change as teeth move (e.g. surfaces further away from the gingival line) could allow better analysis of the lower jaw as well. Using 3D scans of the patient that included other skeletal structures in the head could provide the best reference for measurements.

Performing analyses during treatment is valuable. It allows adjustments to be made to a treatment in progress should it go off course from the original intended plan. The difference between the planned and actual positions of the teeth could be computed to determine the deviation from the plan. This difference can then be used to adjust the plan for the remainder of the treatment. A set of appliances can then be made to correct the deviation and finish executing the treatment plan. Finally, consistently performing these analyses during treatments can provide a useful database that could be used to study treatment progress over time.

DESCRIPTION

Figure 1:
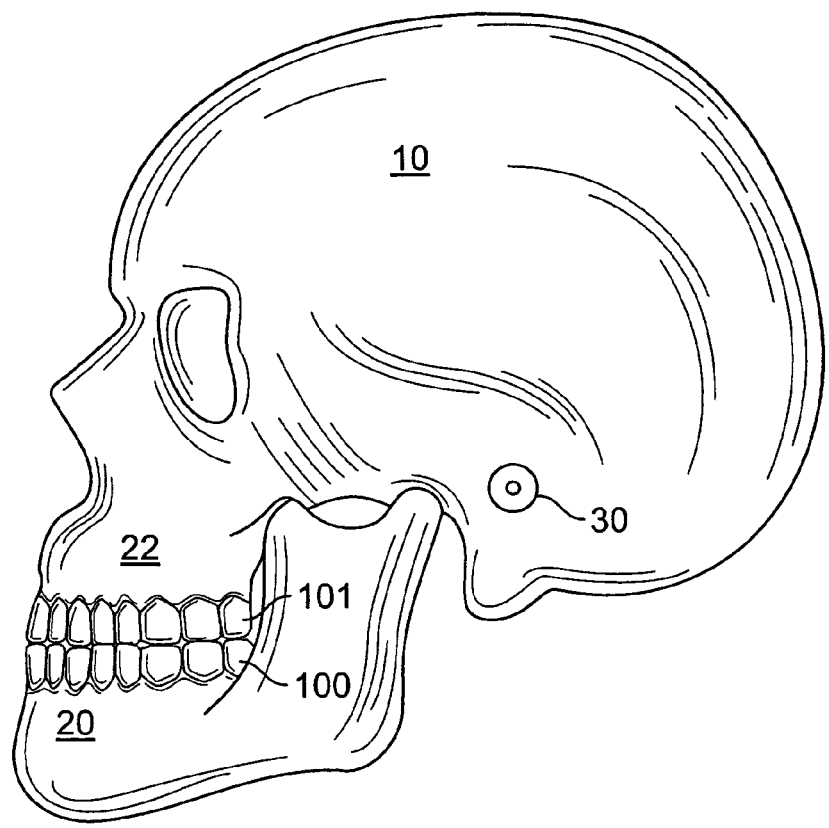
FIG. 1 is an elevational diagram showing the anatomical relationship of the jaws of a patient.

FIG. 1 shows a skull 10 with an upper jaw bone 22 and a lower jaw bone 20. The lower jaw bone 20 hinges at a joint 30 to the skull 10. The joint 30 is called a temporal mandibular joint (TMJ). The upper jaw bone 22 is associated with an upper jaw 101, while the lower jaw bone 20 is associated with a lower jaw 100. A computer model of the jaws 100 and 101 is generated, and a computer simulation models interactions among the teeth on the jaws 100 and 101. The computer simulation allows the system to focus on motions involving contacts between teeth mounted on the jaws. The computer simulation allows the system to render realistic jaw movements that are physically correct when the jaws 100 and 101 contact each other. The model of the jaw places the individual teeth in a treated position. Further, the model can be used to simulate jaw movements including protrusive motions, lateral motions, and "tooth guided" motions where the path of the lower jaw 100 is guided by teeth contacts rather than by anatomical limits of the jaws 100 and 101. Motions are applied to one jaw, but may also be applied to both jaws. Based on the occlusion determination, the final position of the teeth can be ascertained.

Figure 2A:
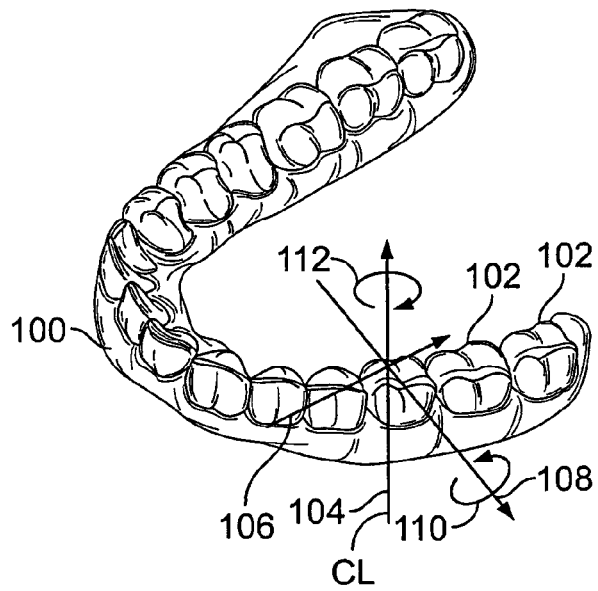
FIG. 2A illustrates in more detail the patient's lower jaw and provides a general indication of how teeth may be moved by the methods and apparatus of the present invention.

Referring now to FIG. 2A, the lower jaw 100 includes a plurality of teeth 102, for example. At least some of these teeth may be moved from an initial tooth arrangement to a final tooth arrangement. As a frame of reference describing how a tooth may be moved, an arbitrary centerline (CL) may be drawn through the tooth 102. With reference to this centerline (CL), each tooth may-be moved in orthogonal directions represented by axes 104, 106, and 108 (where 104 is the centerline). The centerline may be rotated about the axis 108 (root angulation) and the axis 104 (torque) as indicated by arrows 110 and 112, respectively. Additionally, the tooth may be rotated about the centerline, as represented by an arrow 112. Thus, all possible free-form motions of the tooth can be performed.

Figure 2B:
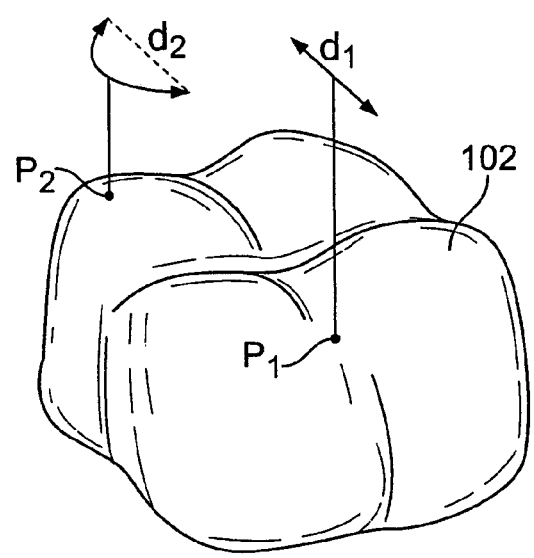
FIG. 2B illustrates a single tooth from FIG. 2A and defines how tooth movement distance is determined.

FIG. 2B shows how the magnitude of any tooth movement may be defined in terms of a maximum linear translation of any point P on a tooth 102. Each point P1 will undergo a cumulative translation as that tooth is moved in any of the orthogonal or rotational directions defined in FIG. 2A. That is, while the point will usually follow a nonlinear path, there is a linear distance between any point in the tooth when determined at any two times during the treatment. Thus, an arbitrary point P1 may in fact undergo a true side-to-side translation as indicated by arrow d1, while a second arbitration point P2 may travel along an arcuate path, resulting in a final translation d2. Many aspects of the present invention are defined in terms of the maximum permissible movement of a point P1 induced on any particular tooth. Such maximum tooth movement, in turn, is defined as the maximum linear translation of that point P1 on the tooth that undergoes the maximum movement for that tooth in any treatment step.

Figure 2C:
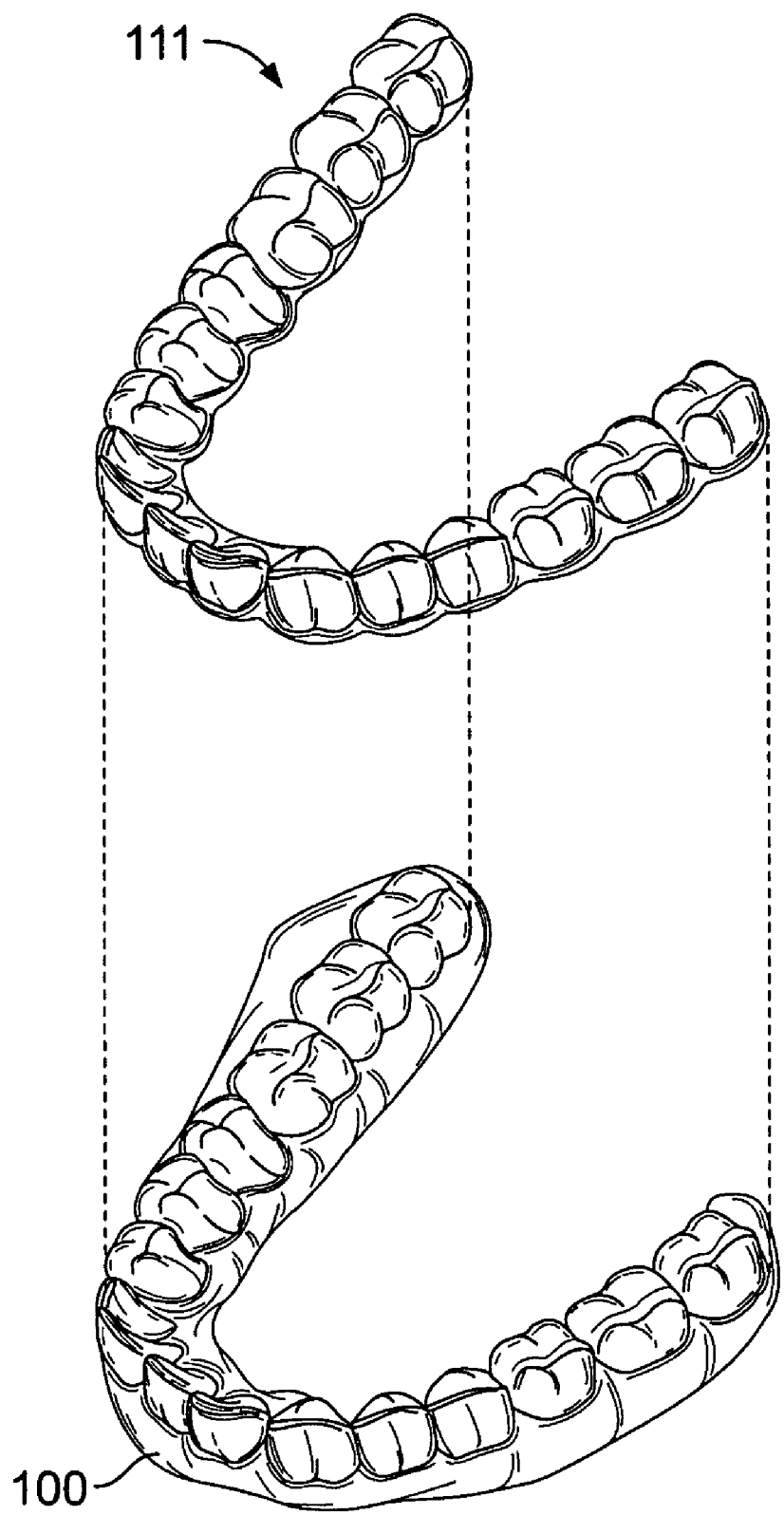
FIG. 2C illustrates the jaw of FIG. 2A together with an incremental position adjustment appliance.

FIG. 2C shows one adjustment appliance 111 which is worn by the patient in order to achieve an incremental repositioning of individual teeth in the jaw as described generally above. The appliance is a polymeric shell having a teeth-receiving cavity. This is described in U.S. application Ser. No. 09/169,036, filed Oct. 8, 1998, now U.S. Pat. No. 6,450,807, which claims priority from U.S. application Ser. No. 08/947,080, filed Oct. 8, 1997, now U.S. Pat. No. 5,975,893, which in turn claims priority from provisional application number 60/050,352, filed Jun. 20, 1997 (collectively the "prior applications"), the full disclosures of which are incorporated by reference.

As set forth in the prior applications, each polymeric shell may be configured so that its tooth-receiving cavity has a geometry corresponding to an intermediate or final tooth arrangement intended for the appliance. The patient's teeth are repositioned from their initial tooth arrangement to a final tooth arrangement by placing a series of incremental position adjustment appliances over the patient's teeth. The adjustment appliances are generated at the beginning of the treatment, and the patient wears each appliance until the pressure of each appliance on the teeth can no longer be felt. At that point, the patient replaces the current adjustment appliance with the next adjustment appliance in the series until no more appliances remain. Conveniently, the appliances are generally not affixed to the teeth and the patient may place and replace the appliances at any time during the procedure. The final appliance or several appliances in the series may have a geometry or geometries selected to overcorrect the tooth arrangement, i.e., have a geometry which would (if fully achieved) move individual teeth beyond the tooth arrangement which has been selected as the "final." Such over-correction may be desirable in order to offset potential relapse after the repositioning method has been terminated, i.e., to permit movement of individual teeth back toward their pre-corrected positions. Over-correction may also be beneficial to speed the rate of correction, i.e., by having an appliance with a geometry that is positioned beyond a desired intermediate or final position, the individual teeth will be shifted toward the position at a greater rate. In such cases, the use of an appliance can be terminated before the teeth reach the positions defined by the appliance.

The polymeric shell 111 can fit over all teeth present in the upper or lower jaw. Often, only certain one(s) of the teeth will be repositioned while others of the teeth will provide a base or an anchor region for holding the appliance 111 in place as the appliance 111 applies a resilient repositioning force against the tooth or teeth to be repositioned. In complex cases, however, multiple teeth may be repositioned at some point during the treatment. In such cases, the moved teeth can also serve as a base or anchor region for holding the repositioning appliance.

The polymeric appliance 111 of FIG. 2C may be formed from a thin sheet of a suitable elastomeric polymer, such as Tru-Tain 0.03 in, thermal forming dental material, available from Tru-Tain Plastics, Rochester, Minn. Usually, no wires or other means will be provided for holding the appliance in place over the teeth. In some cases, however, it will be desirable or necessary to provide individual anchors on teeth with corresponding receptacles or apertures in the appliance 111 so that the appliance can apply an upward force on the tooth that would not be possible in the absence of such an anchor.

Figure 3:
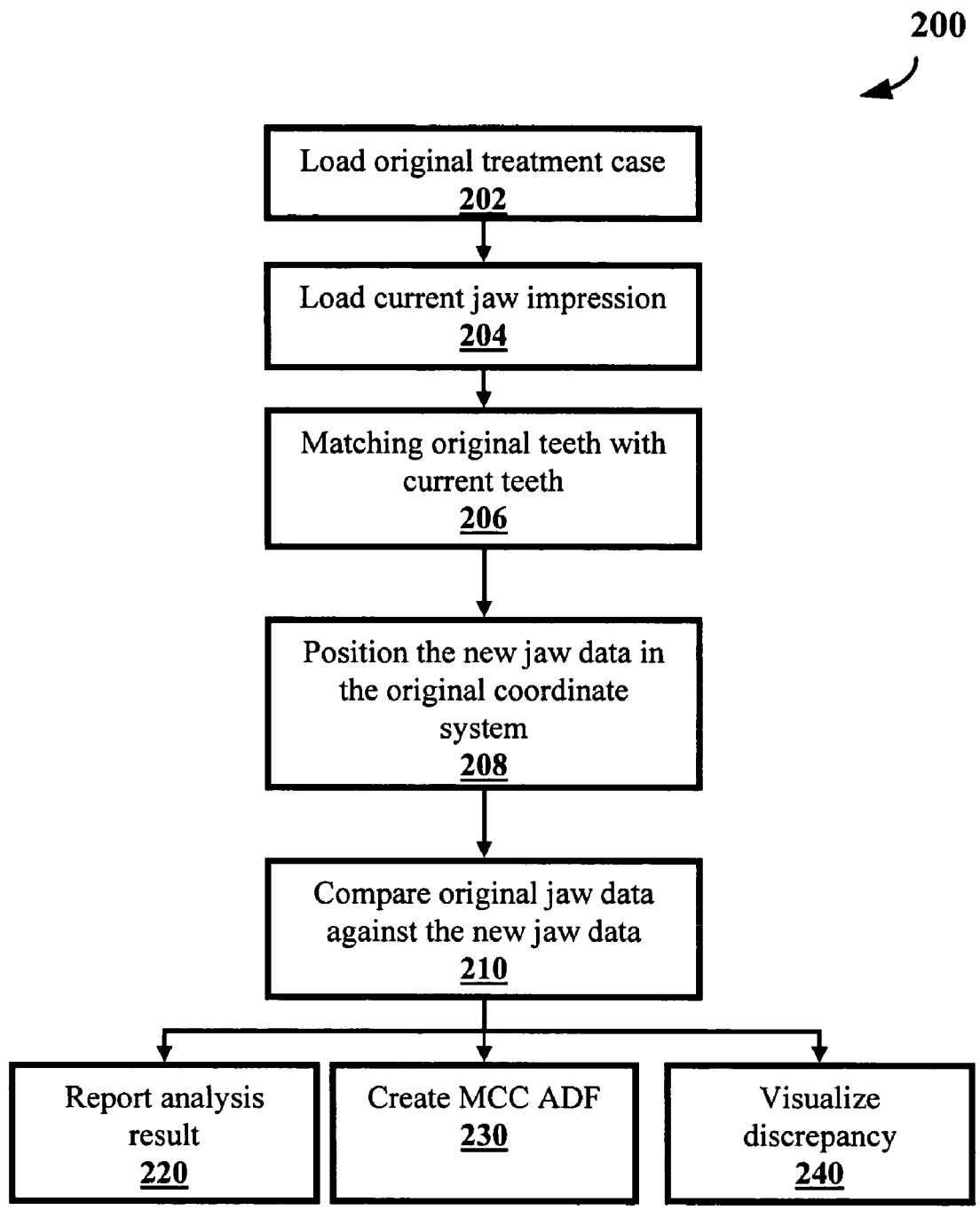
FIG. 3 shows an exemplary bite set process.

FIG. 3 shows an exemplary Treatment Outcome Analysis by Teeth Matching process 200. The process initially creates dental models from the impression and assigns an appropriate coordinate system. Two models are scanned and segmented to create virtual models as described above. Then, a body coordinate system for each tooth is established. The motion of the body coordinate system is used to express the movement of the teeth in a simple way. Next, the process sets a common coordinate system for teeth in the two impressions. This is an important process in the comparison of two models. The impressions are slightly different each time they are taken, and the geometry of a tooth in each impression is also slightly different. In order to compare the movement of teeth in two different impressions, the coordinate system for each tooth must be consistent between the impressions. In order to establish a common coordinate system, the software performs tooth-to-tooth geometric matching. This also determines the relative coordinate transform between the two teeth. In general, given two sets of geometry D1 and D2 (geometry of teeth) they determine the 3D transformation T that will align them. Often the process is called geometry registration. The registration process is accomplished by determining a transformation T that minimizes the discrepancy between D1 and D2. In this work, the discrepancy is defined as the square sum of normal distance between a vertex on D1 and a surface on D2. An iterative optimization method is employed to refine the solution until a best fit match is found.

Once the teeth are aligned, all comparisons are done using the coordinate system of D1. Since the geometry of the teeth may not be exactly the same due to the interproximal modeling and the addition of approximate root geometry, this algorithm only uses surfaces that were present in the original scan data for matching. This data is recorded for each scanned model, and retained as the model is segmented. This process allows the geometry of the original and the new impression to be matched. Differences between the two scans can be due to the quality of the impression or scanning process, or actual wear on the patient's teeth.

The process then establishes a reference frame for measurement. Now that it is possible to determine the relative position of corresponding teeth, it is necessary to establish a frame of reference from which to interpret this relative transform. Having the correct reference frame means that if the two teeth D1 and D2 are in the same position in both models, then T is the identity transform. Once this reference frame is found, the difference in tooth position can be described in relative or absolute terms. To find the absolute movement of the teeth, an external reference frame must be incorporated. Otherwise, only a relative movement of teeth can be calculated.

Once the relative position of the impressions is determined, the movement of each tooth is described as a rigid body transformation. The rigid body transformation is broken down into clinically meaningful directions: distal-mesial, buccal-lingual, and intrusive-extrusive directions. The discrepancy between the surfaces of corresponding teeth can also describe the amount of movement of each tooth.

Referring now to FIG. 3, an original treatment case is loaded (202). Next, a current jaw impression is loaded (204). The teeth data from the original treatment case is compared against the teeth data from the current jaw impression (206). Next, the new jaw data is positioned in the original coordinate system (208). The process 200 then compares the original jaw data against the new jaw data (210). Based on the comparison, the Process 200 generates an analysis report (220). Alternatively, it can create a mid-course correction data file (MCC ADF) (230). In yet another option, the process 200 can generate a visualization showing the discrepancy (240).

The process 206 of FIG. 3 matches data using a tooth by tooth approach. By matching tooth by tooth, the process determines the difference between tooth geometry in two different impressions. Even though the same tooth is scanned, there may be slight differences between impressions. This process reveals the difference between two different impressions.

The process also determines necessary coordinate transformations from the expected 3D coordinates for each tooth to the 3D coordinates for the corresponding tooth in the impression. Once this process is done, the difference of the impression of the individual tooth is ascertained. Based on the information, the process determines tooth alignment data in the current position.

In the next process 208, a second matching operation is performed to determine the position of the new jaw relative to the original coordinate system The current teeth alignment data previously determined is then compared against the current stage. This process positions the scanned jaw impression relative to the original jaw position. Once each tooth is placed, the process can determine the individual difference between the current jaw and original jaw. The process then provides three options: visualize any discrepancy; report the discrepancy in a report or a failure analysis; and create MCC ADF (the file that moves the tooth from its current tooth impression to the expected tooth location).

For example, in one embodiment for visualizing differences between a virtual treatment plan and a scan taken later during treatment, teeth are colored according to a scale to indicate that the tooth is in a different position or orientation in the new scan. Since the tooth movement is represented simply by the movement of the tooth's coordinate system, a comprehensive analysis of the movement can be easily obtained by examining the difference in the coordinate systems of corresponding teeth. The software can display these differences along a variety of dimensions: translation, rotation, surface deviation, and the tooth movement speed metric.

Figure 4:
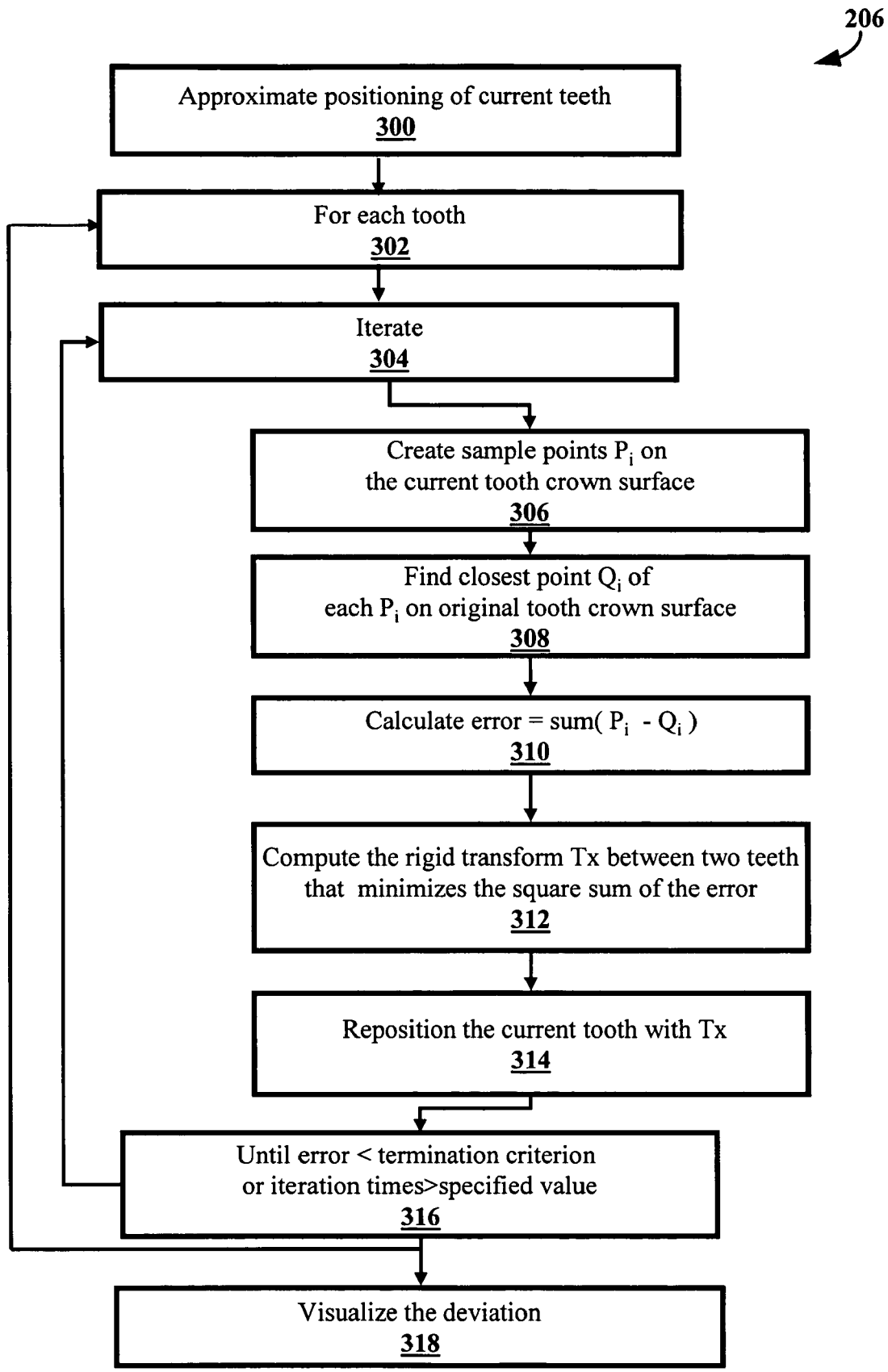
FIG. 4 shows an exemplary process for matching of original teeth data with current teeth data.

Referring now to FIG. 4, the matching of the original teeth data with the current teeth data of box 206 is detailed. In FIG. 4, the process approximates the current positioning of the current teeth (300). Next, the process (304) is iterated for each tooth in 302. The process 304 creates sample points Pi on the current tooth crown surface (306). Next, it finds the corresponding closest point Qi of each Pi on the original tooth crown surface (308). The process then calculates an error of value in this case, the error value is computed as the sum of the distance between Pi and Qi, (310). The process then computes a rigid transformation between two teeth that minimizes the error (312). The current tooth is then repositioned with the transform (314). The process of FIG. 4 is repeated until an error value is less than a predetermined termination criterion or the number of iterations exceeds a predetermined value (316). Finally, the process provides a visual report of the deviation (318).

The process of FIG. 4 positions the current teeth with respect to original teeth using an approximate position. In one embodiment, the process positions two teeth approximately based on each crown center and tooth local coordinate system. Then, for each tooth, a matching operation is performed. The matching operation is an iteration process that minimizes an error value while trying to find the appropriate tooth location. The process finds points on the original tooth crown and finds corresponding points on the current tooth. The process finds each Pi on the current tooth and Qi of the original tooth and calculates the distance between Pi and Qi. The process determines a transformation that minimizes the square sum of these errors. Then the process positions the teeth and starts again. A new point Pi and a new point Qi are selected, and the process finds the difference and determines the transformation that minimizes the error. The above steps are iterated until the error is less than termination criteria or a maximum number of iterations is reached. Then the process graphically illustrates the difference.

Figure 5:
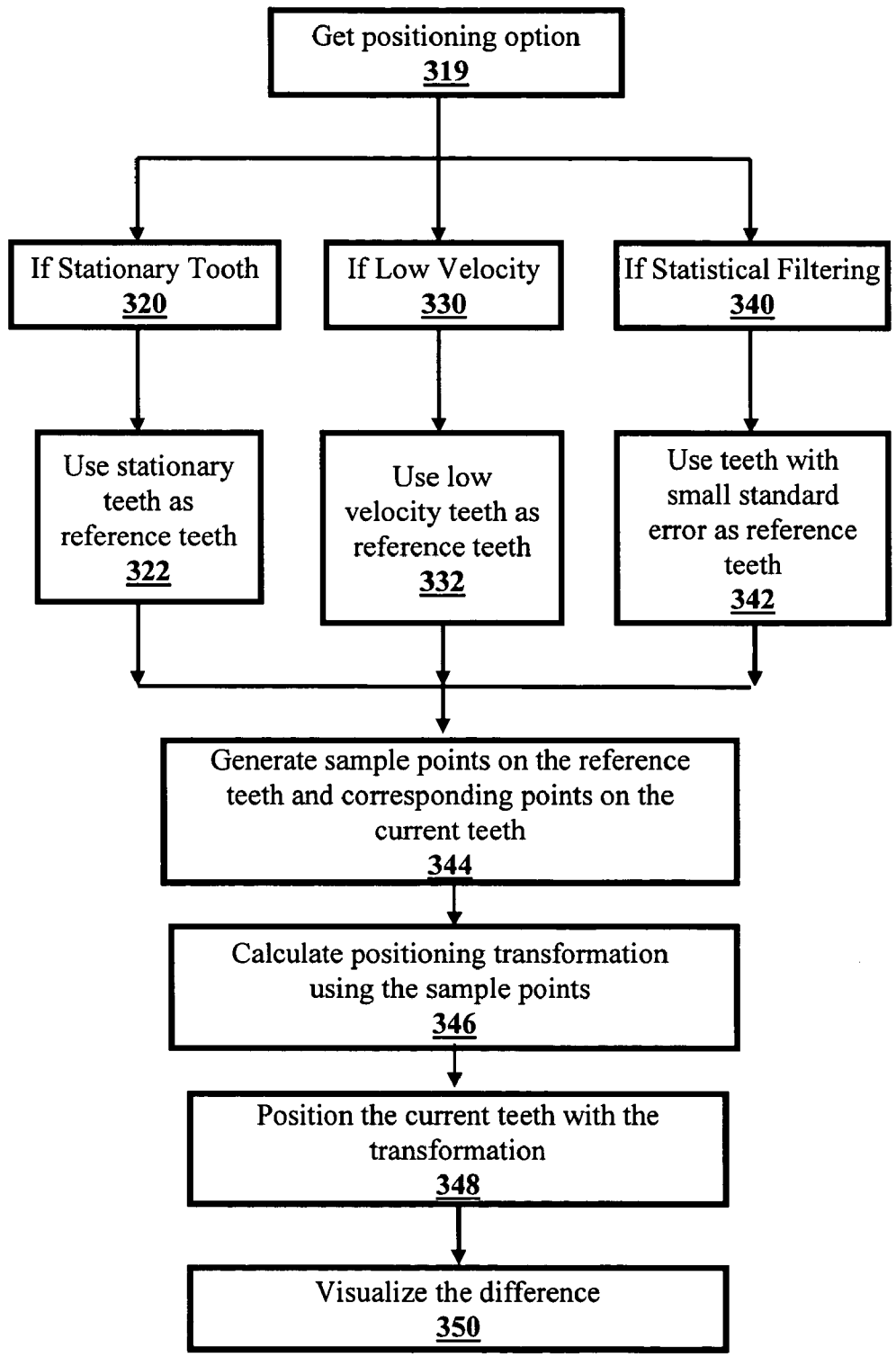
FIG. 5 shows a process for positioning of a newly scanned jaw in the original coordinate system

Turning now to FIG. 5, the positioning of the new jaw in the original coordinate system (208) is detailed. First, the process receives a positioning option from a user (319). If the user specifies stationary teeth option (320), the process uses stationary teeth as a set of reference teeth (322). Alternatively, if the users specify a low velocity model (330), the process uses low velocity teeth as reference teeth (332). From the positioning option 319, if the users specify statistical filtering (340) the process uses teeth with small standard error as reference teeth (342).

From boxes 322,332, or 342, the process generates various sample points on the reference teeth and corresponding points on the current teeth (344). Next, it calculates position transformation using the sample points (346). It processes and positions the current teeth with the transformation (348) and generates a visualization of the difference (350.)

The process provides three different options to position the new jaw in the original coordinate system. User can choose one of the options freely. The first option relies on stationary teeth that are expected to remain stationary throughout the stages. The stationary teeth are then used as a landmark for comparison purposes. Low velocity option allows the user to pick a tooth that moves at a relatively low velocity as a landmark approximation. The statistical filtering approach can be used for selecting small standard error as reference teeth.

Figure 6:
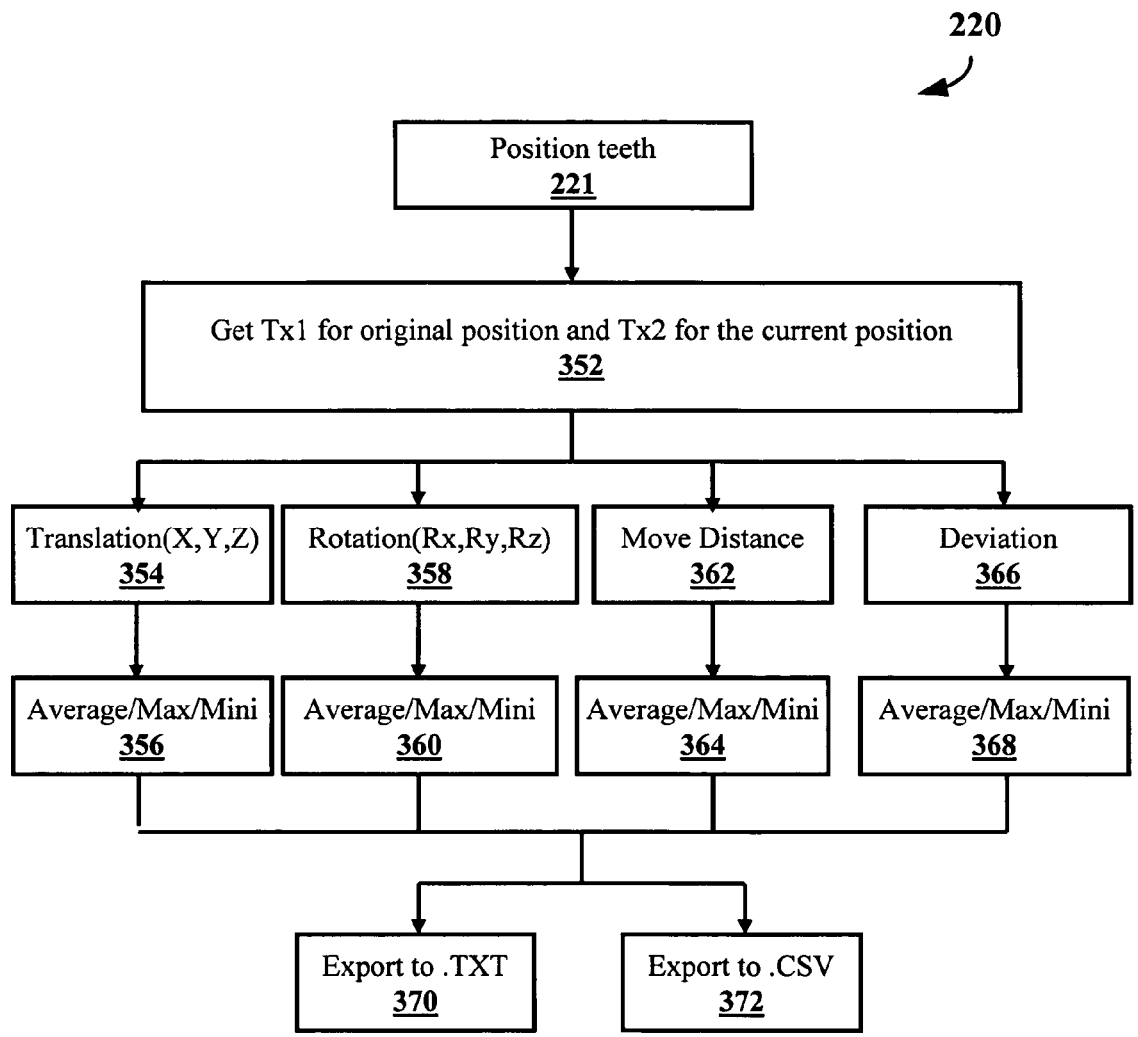
FIG. 6 shows an exemplary report analysis generation process.

Turning now to FIG. 6, the report analysis generation process 220 is detailed. For each individual tooth, the report generates discrepancy information in terms of translation, rotation, movement distance and deviation, and an average for all of the teeth. First, the teeth are positioned (221). Next, the process obtains a first transform for an original position and a second transform for the current position (352). From 352, the process calculates the translation (354) and proceeds to determine the average, maximum and minimum of the translations (356). Alternatively, the process 220 can also calculate rotation for Rx, Ry, Rz (358) and again determines the average, maximum and minimum (360). From 352, the process can also calculate move distance of a tooth (362) and generates a report of the average, maximum, and minimum (364). Additionally, the process 220 can also calculate the deviation (366) and generate a report with the average, maximum and minimum (368). From 356, 360, 364, and 368, the process 220 can generate an export to a text file (TXT) (370) or to a comma separated file (CSV) for the user to perform subsequent analysis (372).

Figure 7:
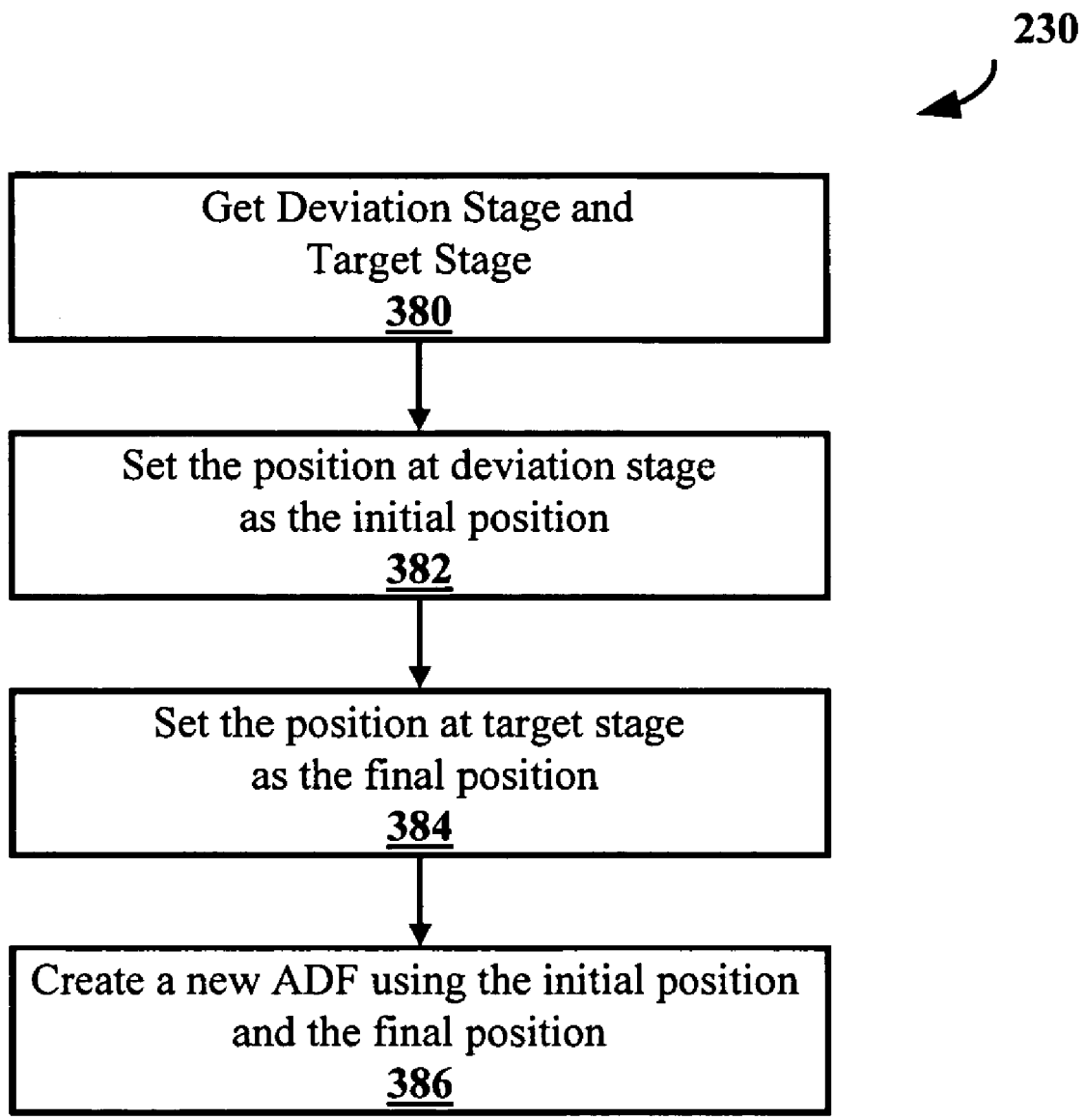
FIG. 7 shows an exemplary process to create reboot appliances in case the patient's teeth are out of synchronization with the treatment plan.

Turning now to FIG. 7, a mid-course correction data file (MCC ADF) create operation 230 is detailed. For treatment plans whose teeth movements have deviated from the treatment plan, the process generates files to bring the treatment back on track.

First, the process obtains the deviation stage and a target stage (380). Next, the process sets the position at a deviation stage as the initial position (382). Additionally, the process sets a position at a target stage as the final position (384). Finally, the process creates a new ADF using the initial position and the final position (386). The process obtains the deviation stage, or the stage where the current impression is taken and where the patient's teeth have gone off the planned path so the aligner fails to fit the teeth. The system also obtains the target stage, which is the stage that the patient's teeth is expected to be. The process uses the current teeth position as the initial position and the target stage of the original treatment plan as the final position.

Figure 8:
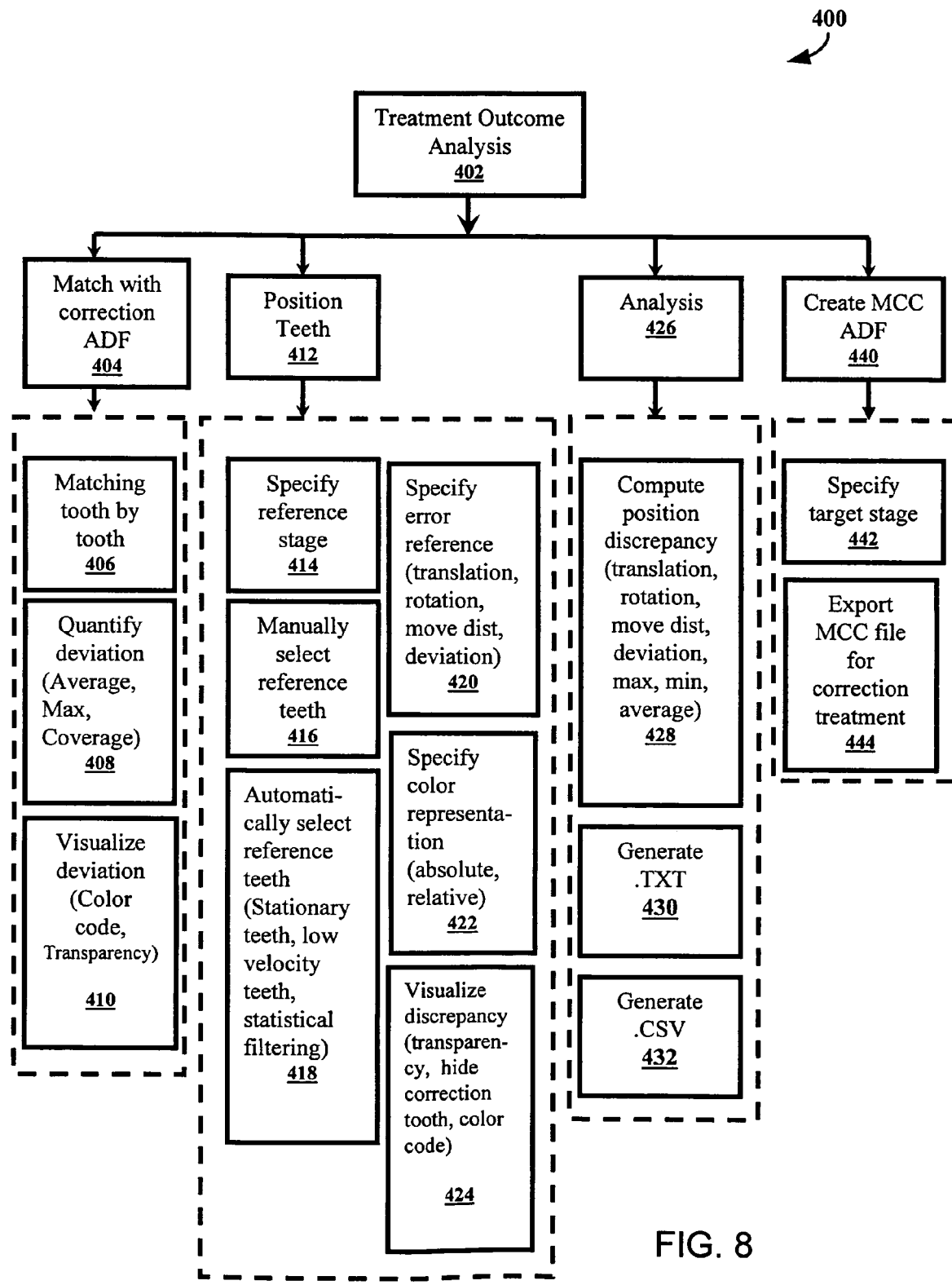
FIG. 8 shows an exemplary functional summary process.

Referring now to FIG. 8, a functional summary process 400 is shown. First, treatment outcome analysis is performed (402). From the treatment outcome analysis, the process 400 performs four operations in sequence. The first operation is to match the treatment with a correction ADF (404). In this operation, the tooth is matched tooth by tooth (406) deviations are quantified (408). The deviation is visualized, for example using color code or transparency values, among others (410). In a second operation where the teeth are positioned (412), the operation includes specifying a reference stage (414), manually selecting a set of reference teeth (416), automatically selecting a set of reference teeth (418), specifying an error reference (420), specifying color representation (422) and visualizing the discrepancy (424).

In the third operation, analysis of the match result is performed (426). First, the position discrepancy is computed (428). Next, a text file is generated (430) or alternatively, a CSV file can be generated (432).

In the final operation, the process 400 creates the MCC ADF (440). In this operation, the target stage can be specified (442) and the result in the MCC file is exported for correction treatment (444).

The above described system matches two different impressions of a patient, one before treatment and one after treatment, the method positions them together in a single three-dimensional space, and calculates the individual tooth movement. This also includes finding the intermediate treatment if the patient's current teeth are off from the intended treatment course.

In this system, there are two different sets of digital models of teeth, the original teeth and the new teeth. First, a comparison of two corresponding teeth in the different set is found by an iterative searching algorithm. The search algorithm finds the relative position of the teeth by minimizing the distance between two superimposed teeth. The matching process is completed throughout the entire teeth of a jaw. After matching the teeth, the shape difference between each of the corresponding teeth, one before treatment and one after treatment, can be identified as a by-product of the matching. This teeth matching provides a foundation for jaw matching so that each new tooth position can be represented relative to the original tooth position. Then, the matched position of individual teeth is used to position the entire jaw. The entire jaw needs an external reference to set the position. A fixed external reference such as rugae in the patient's mouth can be used. If a fixed external reference is not available, some teeth can be used for the reference as well. Once the entire jaw is positioned, the relative movement or discrepancy is precisely calculated. The calculated results are reported in text and also visualized on computer screen.

Figure 9A:
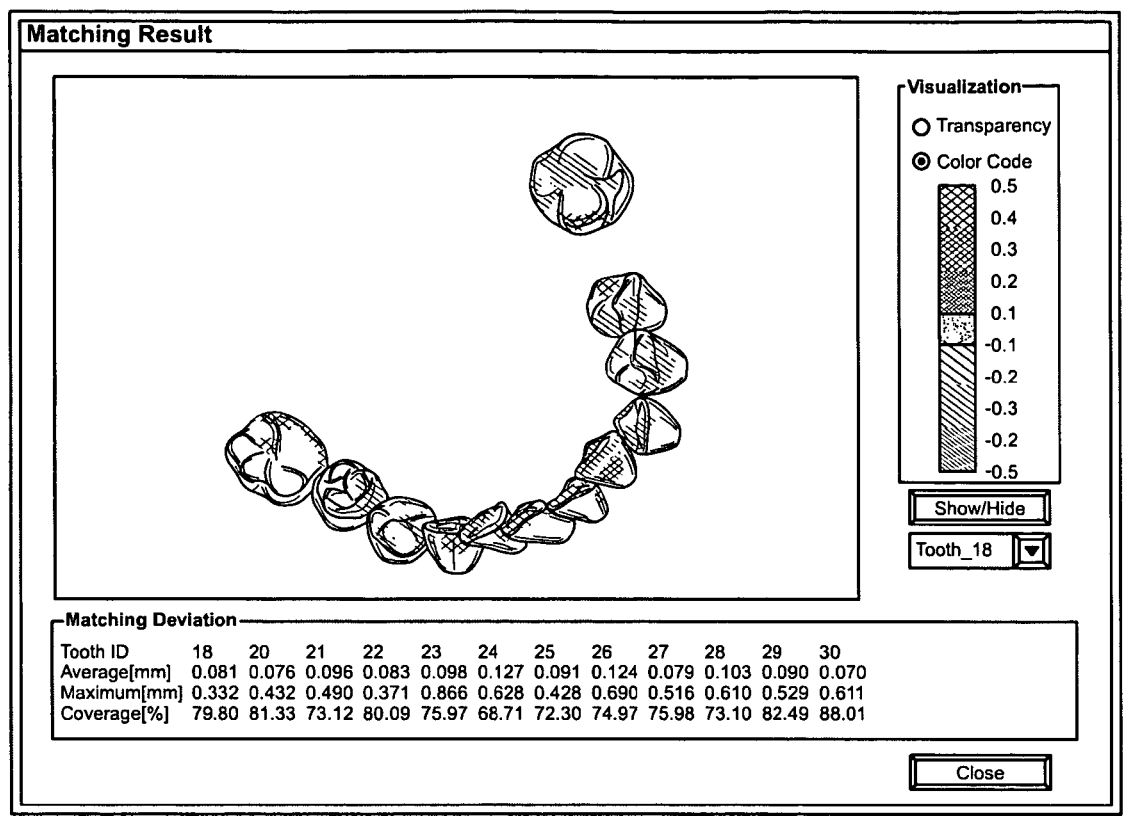
FIGS. 9A and 9B illustrate exemplary shape differences between two corresponding teeth.
Figure 9B:
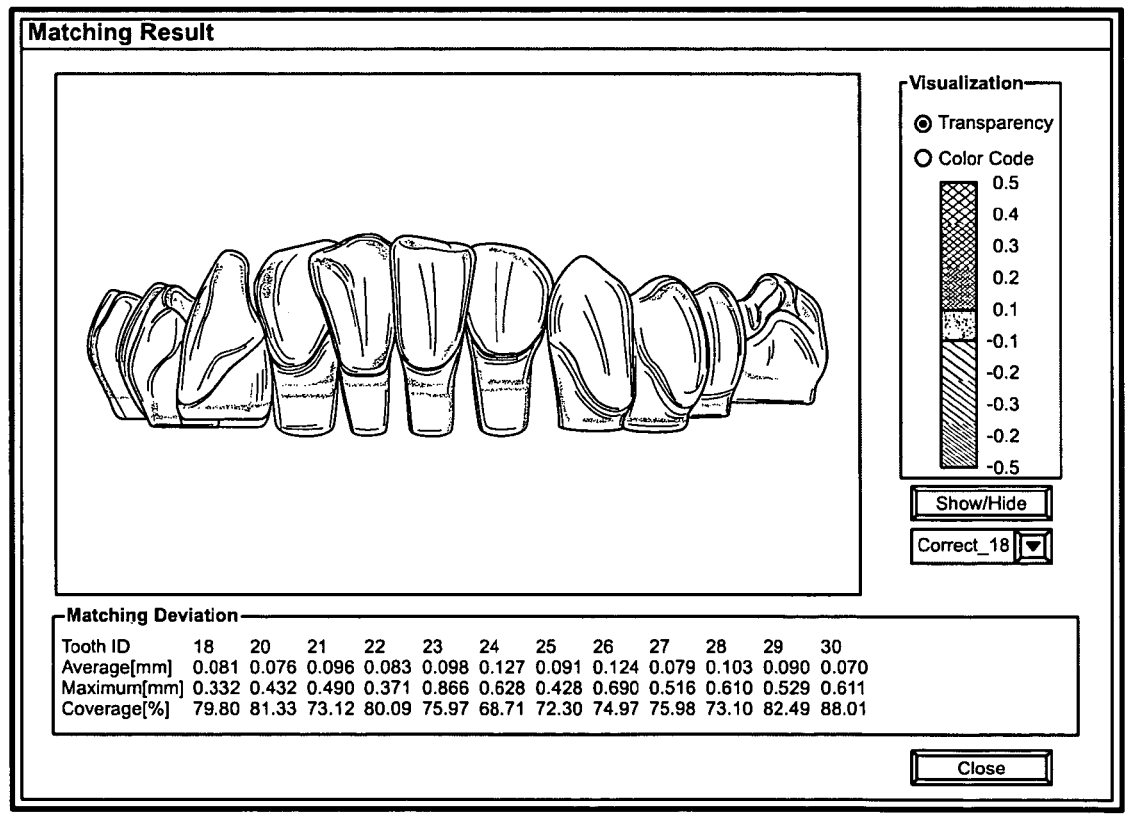

FIGS. 9A and 9B illustrate that the shape difference of two corresponding teeth can be the average deviation, maximum deviation, or coverage percentage, among others. The deviation is defined as the distance between the sampled point on one tooth and its projection point on the other tooth. For displaying the difference in teeth position variance, a color-coded model and a transparent tooth model are used in these exemplary figures.

Figure 10A:
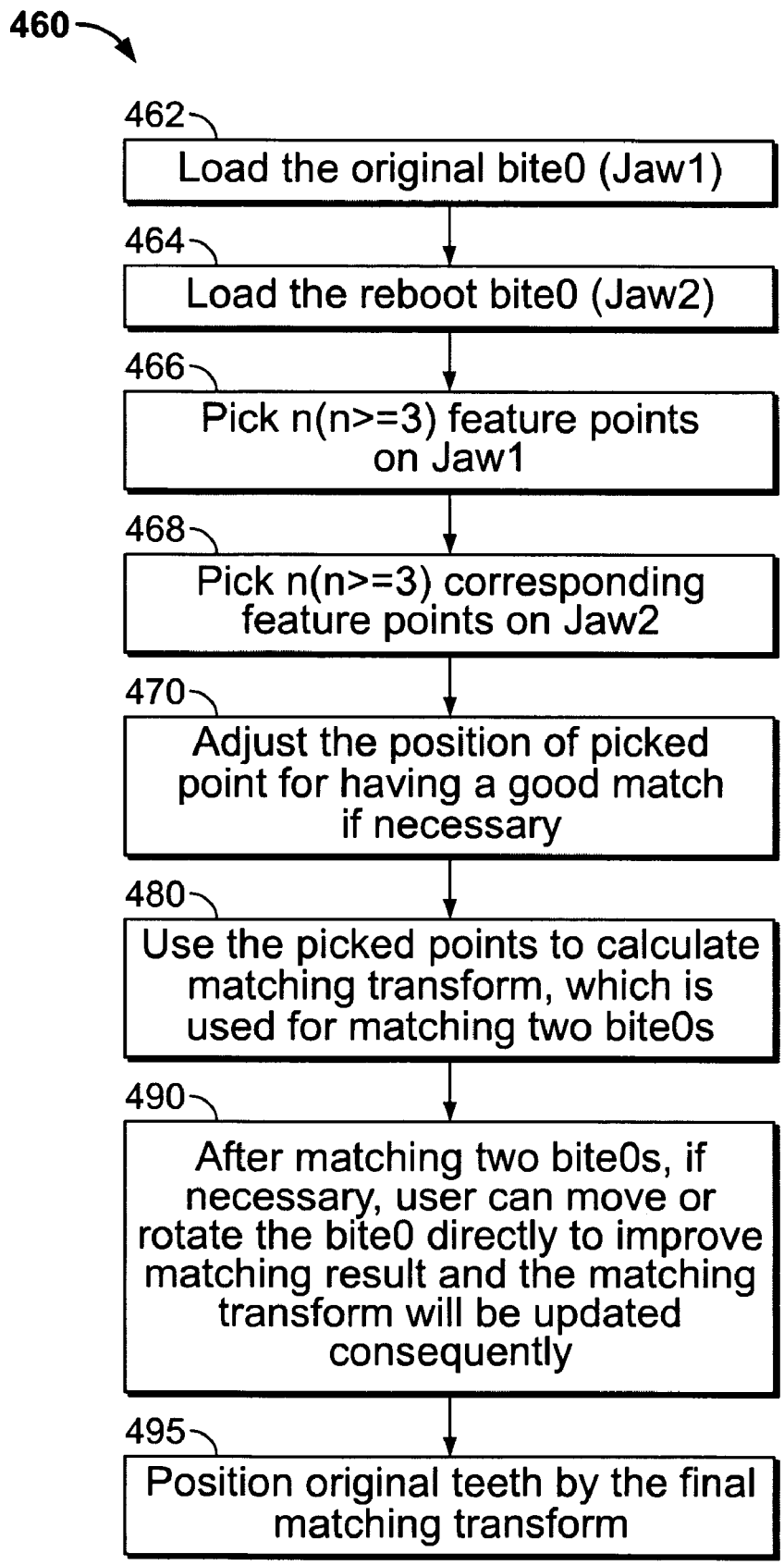
FIG. 10A shows an exemplary embodiment for matching shapes based on rugae.

FIG. 10A shows an exemplary embodiment for matching shapes based on rugae. For matching rugae, the user locates points on the new model, and picks points on the treatment plan model that correspond to those points. These points are then matched such that the models are positioned so they closely align in the regions around the points (i.e. the rugae region), by applying a transform $T_{ref}$ to one of the models. After this reference frame is established, the actual relative transform between teeth can be calculated simply by $T \cdot T_{ref}^{-1}$.

If the rugae region is not available, stationary or slow-moving teeth can be used to establish a reference. For example, if anterior teeth are expected to move, then molars can be used as the reference. Relative movement between the corresponding teeth is then measured compared to the reference teeth. The disadvantage to this technique is that it is limited to relative movements and does not take into account forces that may be moving the reference teeth.

Turning now to FIG. 10A, the process loads the original impression of the teeth or bite0 (Jaw1) (462). Next, the process loads the reboot impression of the teeth (Jaw2) 464. The process selects a plurality of points (for example more than three) feature points on Jaw1 (466) and corresponding feature points on Jaw2 (468). The process then allows the user to adjust the position of picked point for having a good match, if necessary (470). In one embodiment, the user can match the jaws by the marked points on the captured jaw models. If the user wants to modify the position of the marking point, user can move the point by selecting the point and then dragging the point to the desired position. Also, user can delete a point by right clicking the point and then selecting "delete" from the right-click menu.

The process then uses the picked points to calculate a matching transform, which is used for matching two scanned jaw models (480). After matching two scanned jaw models, if necessary, user can move or rotate the jaw model directly to improve matching result and the matching transform will be updated consequently (490). The process then positions the original teeth by the final matching transform 495.

If the rugae region is not available, stationary or slow-moving teeth can be used to establish a reference. For example, if anterior teeth are expected to move, then molars can be used as the reference. Relative movement between the corresponding teeth is then measured compared to the reference teeth. The disadvantage to this technique is that it is limited to relative movements and does not take into account forces that may be moving the reference teeth.

The process of FIG. 10A allows a new scan of a mid-course correction (MCC) case to be best fitted to the original approved treatment. A best-fit comparison of the overlapped models would then allow tooth positions to be analyzed for discrepancies between treatments. The process can be used for positioning the correction teeth together with the original teeth based on the reference stage and reference teeth. The reference teeth can be specified manually or automatically. The discrepancies between the original teeth/position and correction teeth/position can be quantified and visualized. The information in analysis report is focused on the position discrepancies between the original treatment and the new impression. The report is helpful for users to study MCC cases. Based on teeth matching, positioning teeth by matching original bite0 and reboot bite0, or by specified reference stage and teeth, and target stage, MCC ADF can be created. The process can be used to place the treatment back on track without having to completely redo the case. This will get the original treatment away from the deviation without having to waste any materials, and the treatment will be able to use most of the original aligners sent to the doctor, using the additional ones generated to correct the deviation.

Figure 10B:
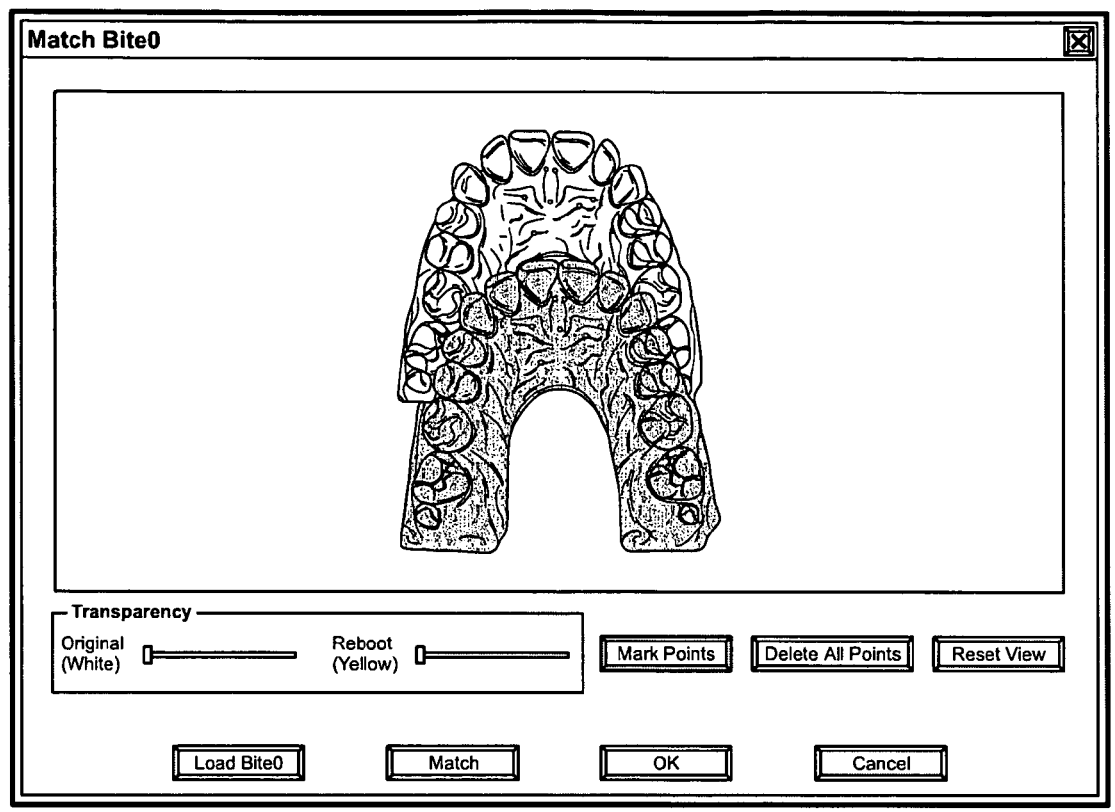
FIGS. 10B–10F show exemplary user interfaces.

FIGS. 10B–10F show exemplary user interfaces. In FIG. 10B, two impression models (bite0s) are loaded into a window. For matching two bite0s, user can match them by marked points on the bite0s. In this embodiment, the user can mark the points on the bite0s. The two groups of points on the bite0s are related by the marking sequence. Besides matching bite0s by marking points, user can manually match them by moving/rotating them.

Figure 10C:
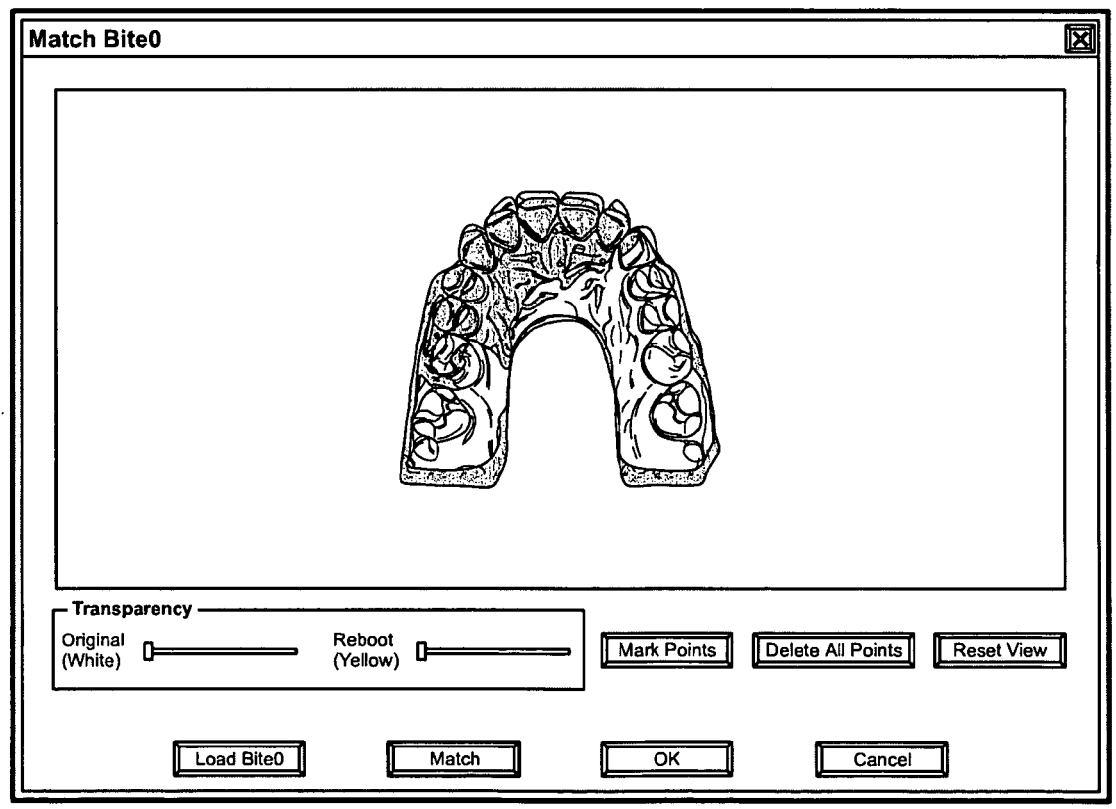

FIG. 10C shows an exemplary user interface after matching the two bite0s. The original teeth will be positioned at a new position based on the bite0 matching. With a transparency slider, the user can make the bite0 transparent so that is helpful for user to observe the matching result. By clicking a Reset View button, user can move the objects' center to the center of the view.

Figure 10D:
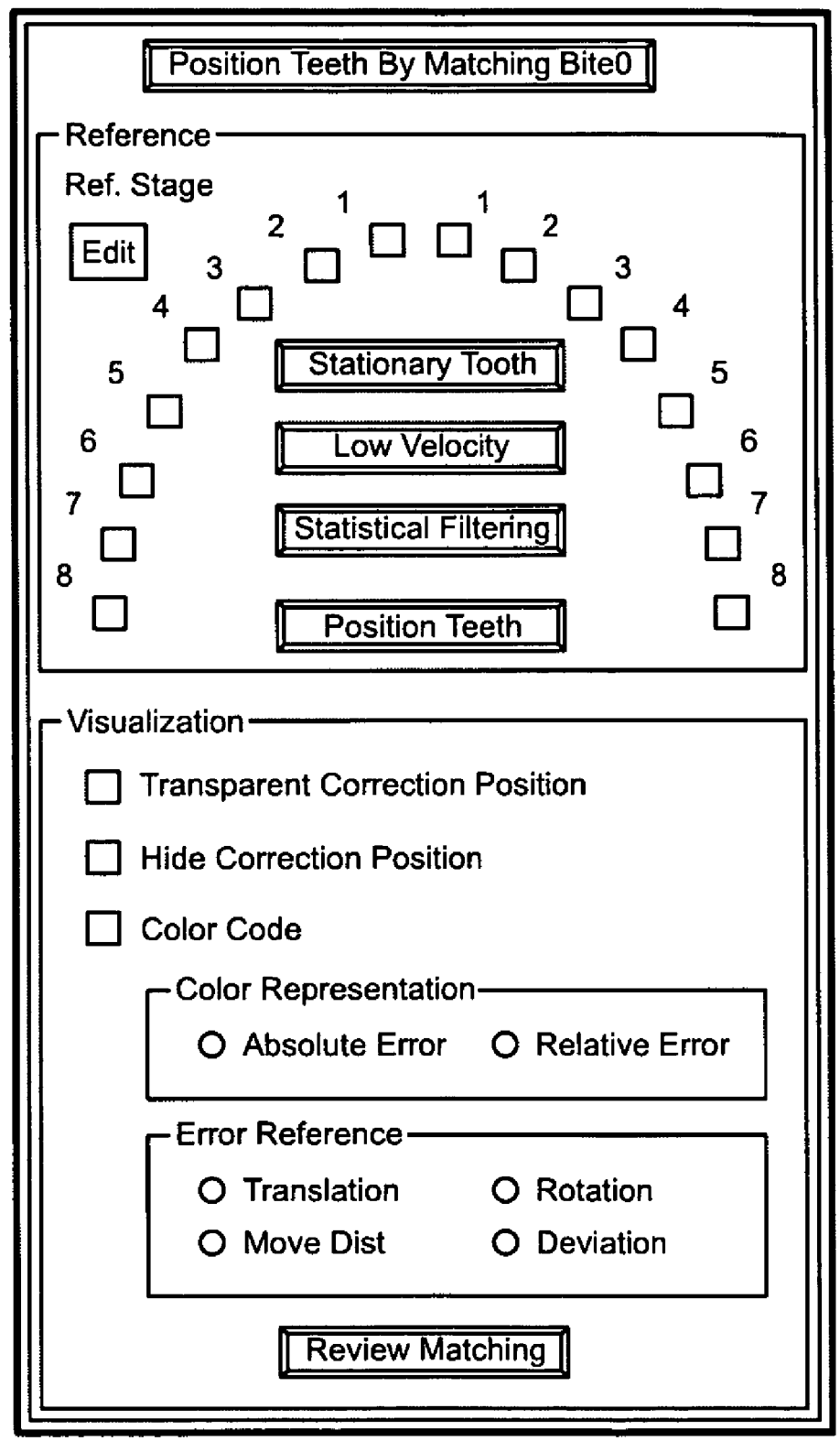

FIG. 10D shows an exemplary user interface where the user can match the bite0s using the Input Reference Stage user interface. There are four approaches for a user to choose reference teeth. If the user wants to select a stationary tooth/teeth as a reference, the user should click the Stationary Tooth button. If the user wants to select a low velocity tooth/teeth as a reference, the user should click the Low Velocity button. If the user wants to use a statistical filtering approach to choose referenced teeth, the user should click the Statistical Filtering button. The user can also choose the teeth by simply clicking the check boxes for the corresponding teeth. After choosing the reference stage and reference teeth, the user can position teeth by clicking the Position Teeth button.

Figure 10E:
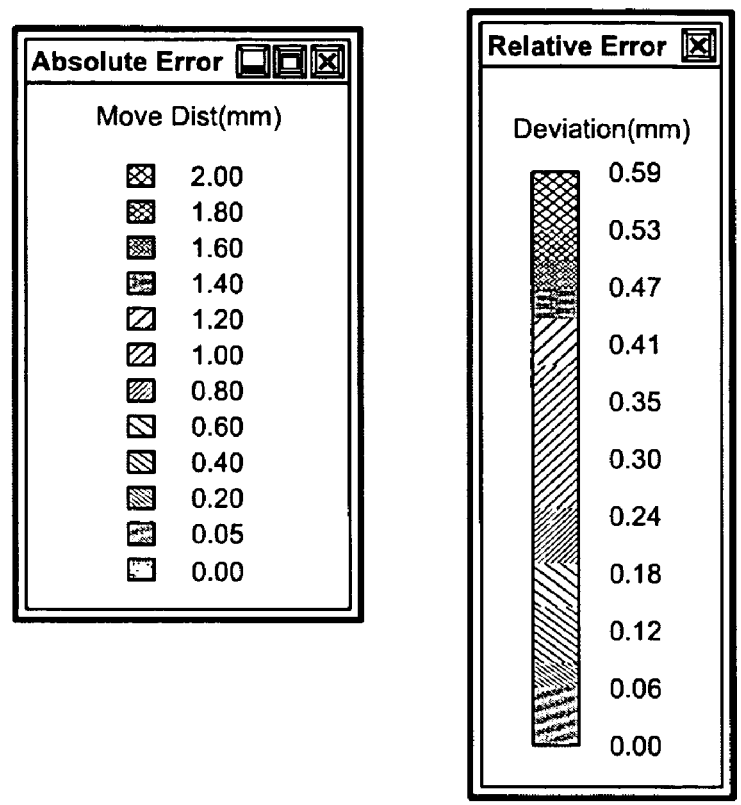
Figure 10E:
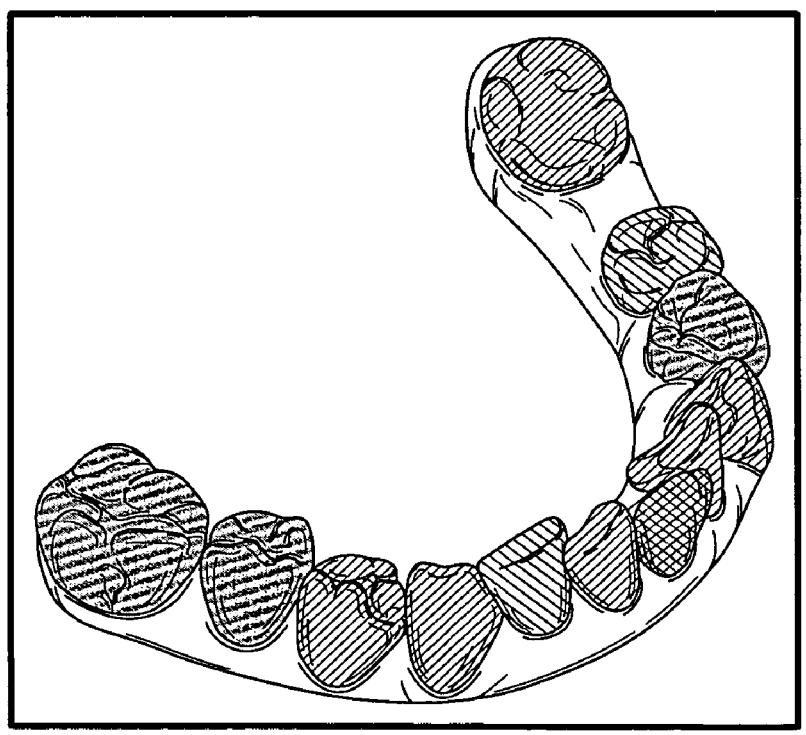

FIG. 10E shows an exemplary illustration of mismatches in the bite0s. In order to visualize the discrepancies between the original position and correction position, the user can check Transparent Correction Position, Hide Correction Position or Color Code. For color code, two color representations are provided: Absolute Error and Relative Error as shown in FIG. 10E. For error reference, the user can choose Translation, Rotation, Move Distance or Deviation as reference. In one embodiment, modeless dialog boxes are used for explaining the meaning of different colors. For example, in FIG. 10E, the left dialog is for absolute error color code, and the right one is for relative error color code.

Figure 10F:
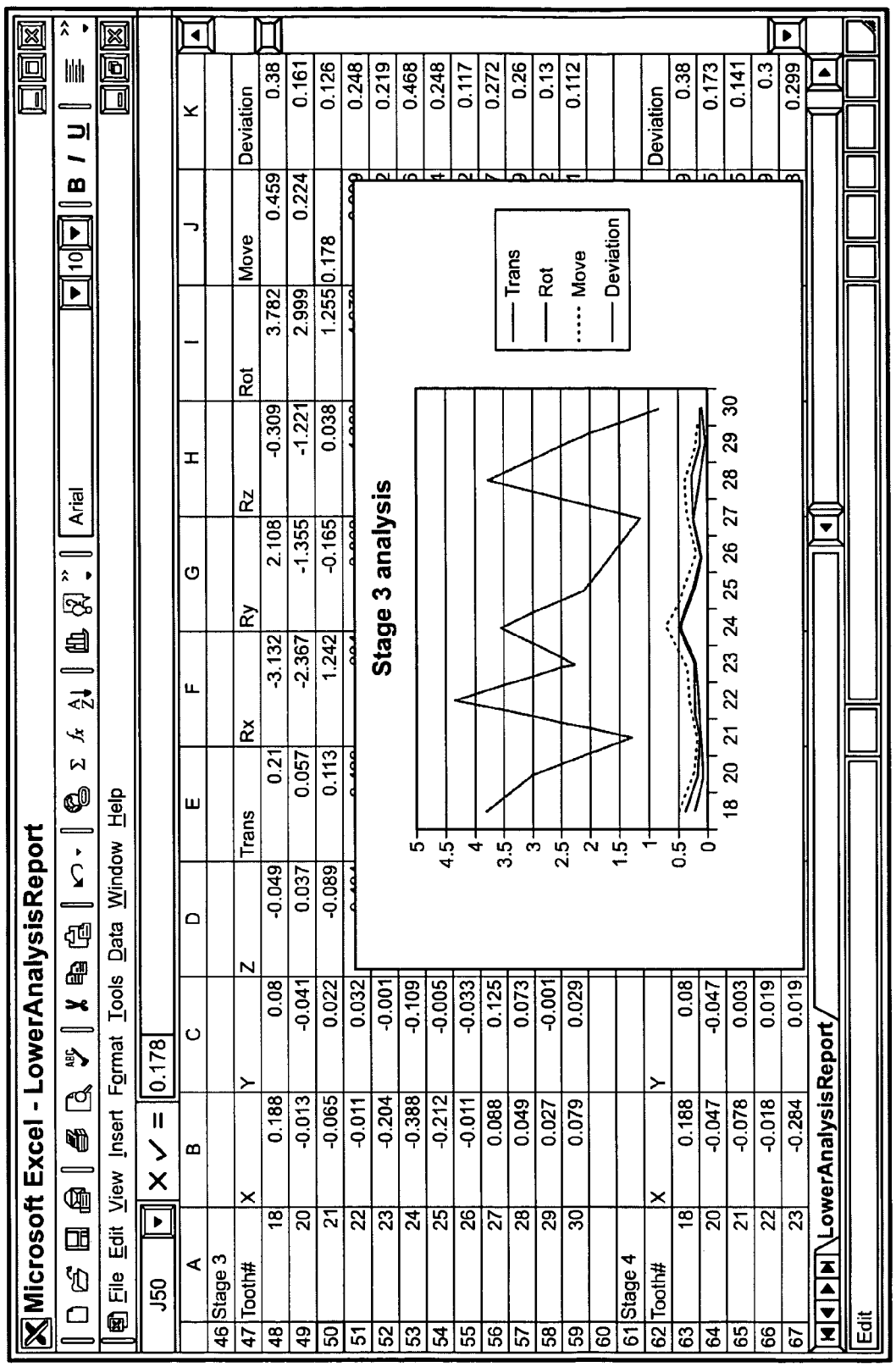

The resulting variances can be exported as text or spreadsheet data for analysis. FIG. 10F shows an exemplary data analysis of teeth positional variances using a spreadsheet analysis.

The system thus provides a 3-dimensional superimposition tool that measures dental changes based on an algorithm of best fit. The software consists of matching the teeth and common coordinates to create the measurements. The teeth matching works by comparing the anatomy of the teeth from the two time points and finds the best fit between them. The software then uses selected internal reference points such as stable teeth to establish a relative position. Stable structures such as the palatal rugae can be used as stable external reference points. After the software superimposes the two images, displacements are measured. Each individual tooth movement can be described by six different measurements (tip, torque, rotation, etc).

This tool allows the opportunity to select which teeth will serve as stable structures to be used for superimposition. The superimposition is done 3-dimensionally and therefore the results can be viewed in the three planes. In addition to superimposing two models—at two time points, this software can also be used to superimpose an existing model with that of any stage of the virtual treatment. This can be used to evaluate how well treatment is progressing according to the projected virtual treatment plan.

Figure 11:
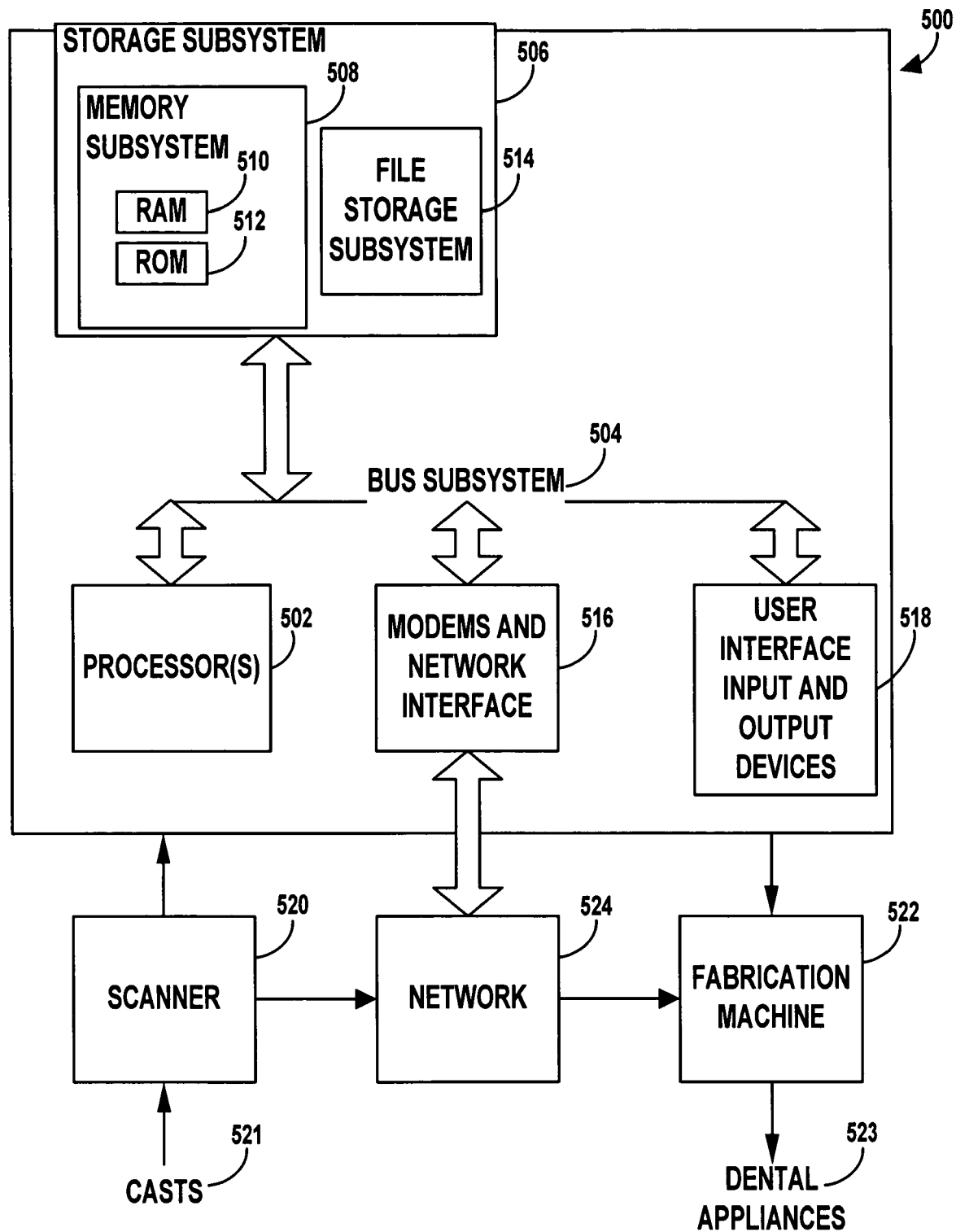
FIG. 11 is a block diagram illustrating a system for generating appliances in accordance with the present invention.

FIG. 11 is a simplified block diagram of a data processing system 500. Data processing system 500 typically includes at least one processor 502 that communicates with a number of peripheral devices over bus subsystem 504. These peripheral devices typically include a storage subsystem 506 (memory subsystem 508 and file storage subsystem 514), a set of user interface input and output devices 518, and an interface to outside networks 516, including the public switched telephone network. This interface is shown schematically as "Modems and Network Interface" block 516, and is coupled to corresponding interface devices in other data processing systems over communication network interface 524. Data processing system 500 may include a terminal or a low-end personal computer or a high-end personal computer, workstation or mainframe. The user interface input devices typically include a keyboard and may further include a pointing device and a scanner. The pointing device may be an indirect pointing device such as a mouse, trackball, touchpad, or graphics tablet, or a direct pointing device such as a touchscreen incorporated into the display. Other types of user interface input devices, such as voice recognition systems, may be used. User interface output devices may include a printer and a display subsystem, which includes a display controller and a display device coupled to the controller. The display device may be a cathode ray tube (CRT), a flat-panel device such as a liquid crystal display (LCD), or a projection device. The display subsystem may also provide nonvisual display such as audio output. Storage subsystem 506 maintains the basic programming and data constructs that provide the functionality of the present invention. The software modules discussed above are typically stored in storage subsystem 506. Storage subsystem 506 typically comprises memory subsystem 508 and file storage subsystem 514. Memory subsystem 508 typically includes a number of memories including a main random access memory (RAM) 510 for storage of instructions and data during program execution and a read only memory (ROM) 512 in which fixed instructions are stored. In the case of Macintosh-compatible personal computers the ROM would include portions of the operating system; in the case of IBM-compatible personal computers, this would include the BIOS (basic input/output system). File storage subsystem 514 provides persistent (nonvolatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web. In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected over various local-area or wide-area network media, including telephone lines. Similarly, the input devices and display need not be at the same location as the processor, although it is anticipated that the present invention will most often be implemented in the context of PCS and workstations. Bus subsystem 504 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system. Scanner 520 is responsible for scanning casts of the patient's teeth obtained either from the patient or from an orthodontist and providing the scanned digital data set information to data processing system 500 for further processing. In a distributed environment, scanner 520 may be located at a remote location and communicate scanned digital data set information to data processing system 500 over network interface 524. Fabrication machine 522 fabricates dental appliances based on intermediate and final data set information received from data processing system 500. In a distributed environment, fabrication machine 522 may be located at a remote location and receive data set information from data processing system 500 over network interface 524.

Various alternatives, modifications, and equivalents may be used in lieu of the above components. Although the final position of the teeth may be determined using computer-aided techniques, a user may move the teeth into their final positions by independently manipulating one or more teeth while satisfying the constraints of the prescription. Additionally, the techniques described here may be implemented in hardware or software, or a combination of the two. The techniques may be implemented in computer programs executing on programmable computers that each includes a processor, a storage medium readable by the processor (including volatile and nonvolatile memory and/or storage elements), and suitable input and output devices. Program code is applied to data entered using an input device to perform the functions described and to generate output information. The output information is applied to one or more output devices. Each program can be implemented in a high level procedural or object-oriented programming language to operate in conjunction with a computer system. However, the programs can be implemented in assembly or machine language, if desired. In any case, the language may be a compiled or interpreted language. Each such computer program can be stored on a storage medium or device (e.g., CD-ROM, hard disk or magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium so configured causes a computer to operate in a specific and predefined manner. Further, while the invention has been shown and described with reference to an embodiment thereof, those skilled in the art will understand that the above and other changes in form and detail may be made without departing from the spirit and scope of the following claims.

What is claimed is:

1. A method for matching computer models of a jaw, the method comprising:
   loading a first computer model of a jaw having teeth in initial positions;
   loading a second computer model of the jaw, wherein positions of at least some of the teeth in the second computer model are different than the initial positions;
   identifying at least one reference point on a region of the first computer model, the region comprising a portion of the jaw other than the teeth;
   identifying a corresponding reference point on a corresponding region of the second computer model for each point identified on the first model;
   matching the region of the first computer model with the corresponding region of the second computer model, using the identified reference points;
   matching the first and second computer models as a whole, using the matched regions; and
   calculating positional differences between the teeth in their initial positions and the teeth in their positions in the second computer model, using the matched regions as non-moving reference regions.

2. The method of claim 1, further comprising:
   displaying the positional differences between the teeth in the first and second models.

3. The method of claim 1, wherein matching the region of the first computer model with the corresponding region of the second computer model comprises:
   placing the first and second computer models in a single coordinate system.

4. The method of claim 1, wherein calculating the positional differences comprises:
   calculating one or more of intrusion, extrusion, translation, rotation, angulation, or inclination of at least some of the teeth in the second computer model, relative to their initial positions in the first computer model.

5. The method of claim 1, further comprising finding a corrective path for moving at least some teeth from their positions in the second computer model to planned treatment teeth positions.

6. The method of claim 1, wherein the matched region is selected from the group consisting of one or more rugae on a palate of the jaw, gingiva, bone, a restoration and an implant.

7. The method of claim 1, further comprising finding a corrective path for moving at least some teeth from their positions in the second computer model to planned treatment teeth positions.

8. The method of claim 7, further comprising instructions to generate one or more appliances based on the corrective path, each appliance having a geometry selected to progressively reposition at least some of a patient's actual teeth.

9. The method of claim 8, wherein the appliances comprise polymeric shell appliances.

10. A system for matching computer models of a jaw, the system comprising:
    means for loading a first computer model of a jaw having teeth in initial positions
    means for loading a second computer model of the jaw, wherein positions of at least some of the teeth in the second computer model are different than the initial positions;
    means for identifying at least one reference point on a region of the first computer model, the region comprising a portion of the jaw other than the teeth;
    means for identifying a corresponding reference point on a corresponding region of the second computer model for each point identified on the first model;
    means for matching the region of the first computer model with the corresponding region of the second computer model, using the identified reference points;
    means for matching the first and second computer models as a whole, using the matched regions; and
    means for calculating positional differences between the teeth in their initial positions and the teeth in their positions in the second computer model, using the matched regions as non-moving reference regions.

11. The system of claim 10, further comprising:
    means for displaying the positional differences between the teeth in the first and second models.

12. The system of claim 10, wherein the means for matching the region of the first computer model with the corresponding region of the second computer model comprises:
    means for placing the first and second computer models in a single coordinate system.

13. The system of claim 10, wherein the means for calculating the positional differences comprises:
    means for calculating one or more of intrusion, extrusion, translation, rotation, angulation, or inclination of at least some of the teeth in the second computer model, relative to their initial positions in the first computer model.

14. The system of claim 10, further comprising means for finding a corrective path for moving at least some teeth from their positions in the second computer model to planned treatment teeth positions.

15. The system of claim 10, wherein the matched region is selected from the group consisting of one or more rugae on a palate of the jaw, gingiva, bone, restoration and an implant.

16. The system of claim 10, further comprising means for finding a corrective path for moving at least some teeth from their positions in the second computer model to planned treatment teeth positions.

17. The system of claim 16, further comprising means for generating one or more appliances based on the corrective path, each appliance having a geometry selected to progressively reposition at least some of a patient's actual teeth.

18. The method of claim 17, wherein the appliances comprise polymeric shell appliances.

19. A tangible computer readable medium containing code for matching computer models of a jaw, the tangible computer readable medium comprising instructions to:
    load a first computer model of a jaw having teeth in initial positions;
    load a second computer model of the jaw, wherein positions of at least some of the teeth in the second computer model are different than the initial positions;
    identify at least one reference point on a region of the first computer model, the region comprising a portion of the model other than the teeth;
    identify a corresponding reference point on a corresponding region of the second computer model for each point identified on the first model;

march the region of the first computer model with the corresponding region of the second computer model, using the identified reference points;

match the first and second computer models as a whole, using the matched regions; and calculate positional differences between the teeth in their initial positions and the teeth in their positions in the second computer model, using the matched regions as non-moving reference regions.

20. The medium of claim 19, further comprising instructions to:

display the positional differences between the teeth in the first and second models.

21. The medium of claim 19, further comprising instructions to:

place two jaw impressions in a single coordinate system.

22. The medium of claim 19, further comprising instructions to:

calculate one or more of intrusion, extrusion, translation, rotation, angulation, or inclination of at least some of the teeth in the second computer model, relative to their positions in the first computer model.

23. The medium of claim 19, further comprising instructions to find a corrective path for moving at least some teeth from their positions in the second computer model to planned treatment teeth positions.

24. The medium of claim 23, further comprising instructions to generate one or more appliances based on the corrective path, each appliance having a geometry selected to progressively reposition at least some of a patient's actual teeth.

25. The medium of claim 24, wherein the appliances comprise polymeric shell appliances.

26. The medium of claim 19, wherein the watched region is selected from the group consisting of one or more rugae on a palate of the jaw, gingiva, bone, a restoration, and an implant.

* * * * *